United States Patent
Uemura et al.

(10) Patent No.: US 7,282,579 B2
(45) Date of Patent: Oct. 16, 2007

(54) SERINE PROTEASE BSSP6

(75) Inventors: Hidetoshi Uemura, Hyogo (JP); Akira Okui, Nara (JP); Katsuya Kominami, Osaka (JP); Nozomi Yamaguchi, Kyoto (JP); Shinichi Mitsui, Kyoto (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 195 days.

(21) Appl. No.: 11/055,989

(22) Filed: Feb. 14, 2005

(65) Prior Publication Data

US 2005/0170415 A1 Aug. 4, 2005

Related U.S. Application Data

(62) Division of application No. 09/856,320, filed as application No. PCT/JP99/06476 on Nov. 19, 1999, now Pat. No. 6,921,658.

(30) Foreign Application Priority Data

Nov. 20, 1998 (JP) .................................. 10-347802

(51) Int. Cl.
C07H 21/04 (2006.01)
C12N 9/64 (2006.01)
C12N 1/20 (2006.01)
C12N 15/63 (2006.01)

(52) U.S. Cl. ................ 536/23.2; 435/226; 435/252.33; 435/325; 435/254.2; 435/320.1

(58) Field of Classification Search ...................... None
See application file for complete search history.

(56) References Cited

U.S. PATENT DOCUMENTS

| | | | |
|---|---|---|---|
| 5,772,996 A | 6/1998 | Atkinson | |
| 5,840,871 A | 11/1998 | Hillman et al. | |
| 6,075,136 A * | 6/2000 | Tang et al. | 536/23.1 |
| 6,100,059 A | 8/2000 | Southan | |
| 6,232,456 B1 | 5/2001 | Cohen | |
| 6,331,427 B1 | 12/2001 | Robison | |
| 6,420,157 B1 | 7/2002 | Darrow et al. | |

FOREIGN PATENT DOCUMENTS

| WO | WO98/32865 | 7/1998 |
|---|---|---|
| WO | WO98/54963 | 12/1998 |
| WO | WO99/31236 | 6/1999 |
| WO | WO99/41387 | 8/1999 |
| WO | WO99/49055 | 9/1999 |

OTHER PUBLICATIONS

Galye et al, Identification of regions in interleukin-1 alpha important for activity. ☐☐J Biol Chem. Oct. 15, 1993;268(29):22105-11.*

Whisstock et al, Prediction of protein function from protein sequence and structure.☐☐Q Rev Biophys. Aug. 2003;36(3):307-40. Review.*

Issued Patents database US 6,232,456 Cohen et al May 15, 2001 SEQ ID No: 8. Alignment with SEQ ID No. 1.*

GenEmbl database Accession No. AB012917 Toshida et al from cDNA cloning and expression of a novel serine protease, TLSP. Biochim Biophys Acta. Aug. 20, 1998(1399(2-3):225-8. Alignment with SEQ ID No. 1.*

Issued_Patents_NA database U.S. Appl. No. 09/025,059, filed Feb. 17, 1998, Tang et al. Alignment with SEQ ID No. 1.*

USPTO in house alignment from Tang et al, US 6,075,136 Jun. 13, 2000 SEQ ID No. 1, Alignment with SEQ ID No. 2.*

Tsugita A., Developments in protein microsequencing. Adv Biophys. 1987;23:81-113. Review.*

Brewer et al., "Human secreted protein gene 179 clone HETBX14", WO9854963-A2, EMBL Acc# AAV84589 (1998).

Bruck et al., "New human serine proteae CASB12, for treatment, prevention and diagnoisi of cancer and autoimmune diseases", WO9949055-A1 (1999). EMBL Acc# AAY2440 Alignment with SEQ ID No. 2.

Chen et al., "Expression and activity-dependent changes of a novel limbic-serine protease gene in the hippocampus", *The Journal of Neuroscience*, 15(7)5088-5097 (1995).

Davies et al., "Serine proteases in rodent hippocampus", *J. Biol. Chem.*, 273(36)23004-11 (1998a). EMBL Acc#AJ005641.

Maniatis et al., Hybridization to nitrocellulose filters in: Molecular cloning, *A laboratory manual*, 326-389 (1982).

Marra et al., "The WashU-HHMI mouse EST project", EMBL Acc#AA073833 Alignment with SEQ ID No. 2 (1996).

U.S. Ser. No. 610059, filed 2000, Southan et al. SEQ ID No. 1. Alignment with SEQ ID No. 2.

Tang et al., "New prostate-associated serum protease . . . " WO9941387-A2, EMBL Acc#AAZ30222 (1999a), Alignment with SEQ ID No. 2.

Yamashiro et al., "Molecular cloning of a novel trypsin-like serine protease preferentially expressed in brain", *Biochimica et Biophysica Acta*, (1997), vol. 1350, pp. 11-14.

Yoshida et al., cDNA cloning and expression of a novel serine protease, TLSP[1], *Biochimica et Biophysica Acta*, 1399:225-228 (1998).

Yoshida et al., "Sequence analysis and expression of human neuropsin cDNA and gene", *Gene*, 213:9-16 (1998).

Yoshida et al., "cDNA cloning and expression of a novel serine protease", TLSP, *Biochim Biophys Acta.*, 1399(2-3)225-8 (1998a). Alignment with SEQ ID No. 2.

* cited by examiner

*Primary Examiner*—Sheridan Swope
(74) *Attorney, Agent, or Firm*—Browdy & Neimark, PLLC

(57) ABSTRACT

There are provided a polynucleotide encoding human BSSP6 serine protease and a vector and transformed host cells containing this human BSSP6 serine protease encoding polynucleotide.

3 Claims, 13 Drawing Sheets

FB: fetus brain
AB: adult brain
AH: adult hippocampus
SG: salivary gland
TG: thyroid gland
MG: mammary gland
Lu: lung
Ki: kidney
Li: liver
Pa: pancreas
Sl: small intestine
Pr: prostate
Te: testicle
Pl: placenta V: mutant hBSSP6

N: normal hBSSP6 plasmid PC  DU  LN  Te  Lu  FB  AH

PC: PC-3

DU: DU145

LN: LNCaP

Te: testicle

Lu: lung

FB: fetus brain

AH: adult hippocampus

SERINE PROTEASE BSSP6

REFERENCE TO RELATED APPLICATIONS

The present application is a divisional of application Ser. No. 09/856,320, filed May 21, 2001, and now issued as U.S. Pat. No. 6,921,658, which is a national stage under 35 U.S.C. §371 of international application PCT/JP99/06476, filed Nov. 19, 1999, which designated the United States, and which application was not published in the English language.

FIELD OF THE INVENTION

The present invention relates to isolated polynucleotides of human and mouse serine proteases (hereinafter referred to as "hBSSP6" and "mBSSP6", respectively, and, in case no differentiation thereof from each other is needed, simply referred to as "BSSP6"), and their homologous forms, mature forms, precursors and polymorphic variants as well as a method for detecting thereof. Further, it relates to hBSSP6 and mBSSP6 proteins, compositions containing hBSSP6 and mBSSP6 polynucleotides and proteins, as well as their production and use.

BACKGROUND OF THE INVENTION

In general, proteases are biosynthesized as inactive precursors. They undergo limited hydrolysis in molecules to convert into activated type proteases. In so far as enzymes are proteases, they have an activity for hydrolyzing a peptide bond, while their action modes are varied according to kinds of proteases. According to a particular kind of catalytic site, proteases are divided into serine proteases, cysteine proteases, aspartate proteases, metal proteases and the like. Proteases of each kind have a variety of properties, ranging from a protease having general digestive properties to a protease having various regulatory domains and strict substrate specificity, thereby specifically hydrolyzing only characteristic proteins.

Further, proteins undergo various processing even after translation to produce active proteins. In many secretory proteins, a protein are first synthesized on the ribosome in cytoplasm as an inactive precursor (pro-form) which comprises an active protein bearing at the N-terminus thereof a peptide of about 15 to 60 amino acids responsible for secretion (secretory signal). This peptide region is concerned with the mechanism for passing through the cell membrane and is removed upon cleavage by a specific protease during the passage through the membrane, in almost all the cases, to produce the mature type protein. A secretory signal has a broad hydrophobic region comprising hydrophobic amino acids in the middle of the sequence, and basic amino acid residues at a site close to the N-terminus. A secretory signal is a synonym of a signal peptide. In addition, in some proteins, a peptide moiety which functions as a secretory signal is further attached to the N-terminus of the inactive precursor. Such a protein is called a prepro-protein (prepro-form).

For example, trypsin is present as a prepro-form immediately after translation into amino acids. After being secreted from cells, it is present as a pro-form and is converted into active trypsin in duodenum upon limited hydrolysis by enteropeptidase or by trypsin itself.

The optimal pH range of serine proteases is neutral to weak alkaline and, in general, many of them have a molecular weight of about 30,000 or lower. All proteases of blood coagulation, fibrinolysis and complement systems having a large molecular weight belong to trypsin-like serine proteases. They have many regulator domains and form a protease cascade which is of very importance to reactions in a living body.

Recently, cDNAs and amino acid sequences of many novel proteases have been determined by PCR for consensus sequences of serine proteases using oligonucleotide primers. According to this method, novel proteases have been found by various researchers such as Yamamura et al. (Yamanura, Y et al., Biochem. Biophys. Res. Commun., 239, 386, 1997), Gschwend, et al. (Gschwend, T. P. et al., Mol. Cell. Neurosci., 9. 207, 1997), Chen et al. (Chen, Z-L, et al., J. Neurosci., 15, 5088, 1995) and others.

SEQ ID NO: 3 of JP 9-149790 A discloses neurosin as a novel serine protease. Neurosin has also been reported in Biochimica et Byophysica Acta, 1350, 11-14, 1997. By this, there is provided a method for mass production of neurosin using the serine protease gene and a method for screening specific inhibitors using the enzyme. In addition, the screening method has been shown to be useful for screening medicines for treating various diseases.

Serine proteases expressed in a brain-nerve system such as neurosin are considered to play various roles in the brain-nerve system. Therefore, there is a possibility that isolation of a gene encoding a novel protease expressed in a brain-nerve system and production of a protein using the gene would be useful for diagnosis or treatment of various diseases related to the brain-nerve system.

Nowadays, in general, clinical diagnosis of Alzheimer's disease is conducted based on the diagnosis standard of DSM-IIIR and NINCDS-ADRDA (Mckhann, G. et al., Neurology, 34. 939, 1994) or the diagnosis standard of DSM-IV (American Psychiatric Association; Diagnostic and statistical manuals of mental disorders, 4th ed., Washington D.C., American Psychiatric Association, 1994). However, these standards are conditioned by decline of recognition functions which causes a severe disability in a daily life or a social life. Then, it is pointed out that the diagnosis is less scientific objectivity because the diagnosis may be influenced by the level of an individual's social life and further the specialty and experience of a physician who diagnoses particular conditions. In addition, definite diagnosis of Alzheimer's disease is conducted by pathohistological analyses and, in this respect, substantial inconsistency between clinical diagnosis and autopsy diagnosis is pointed out.

At present, image diagnosis is employed as a supplemental means in clinical diagnosis of Alzheimer's diagnosis and it is possible to analyze brain functions, for example, decline of metabolism and atrophy in specific sites such as hippocampus, parietal lobe of cerebral cortex and the like which are specific for Alzheimer's disease by PET and SPECT. However, to define Alzheimer's disease based on lowering of a blood flow from parietal lobe to temporal lobe is very dangerous. In addition, there is few report showing that MRS testicle useful for patients with dementia including those of Alzheimer's disease. Further, although CT-MRI image diagnosis is used, a lesion of white matter such as atrophy of brain, PVL or the like is not specific for Alzheimer type dementia. Since it has been reported that atrophy of brain proceeds as getting older, the above observation is not necessarily found in Alzheimer type dementia. Furthermore, since an image obtained by MRI varies according to strength of a magnetic field, performance of an apparatus and imaging conditions, numerical data obtain in different facilities cannot be compared with each other except atrophic change. In addition, there is a limit to image measurement. Further, enlargement of ventricle can be recognized in vascular dementia cases and there are cases wherein atrophy of hippocampus is observed after ischemia of basilar artery.

Under these circumstances, many researchers have requested to develop biological diagnosis markers as a means for providing better precision and objectivity for clinical diagnosis of Alzheimer's disease. At the same time, the following important roles in the future will be expected.

1) Objective judgment system of effect of medicaments for treating Alzheimer's disease.

2) Detection of Alzheimer's disease before a diagnosis standard is met, or disease conditions are manifested.

Further, data obtained in different facilities can be compared with each other by using the same diagnosis marker. Therefore, development of biological diagnosis markers is recognized to be a most important field among fields of Alzheimer's disease studies and its future prospects will be expected. Approaches to development of biological diagnosis markers up to now are divided into that based on constitute components of characteristic pathological changes of Alzheimer's disease such as senile plaque and neurofibril change, and an approach based on other measures. Examples of the former include cerebrospinal fluid tau protein, Aβ and its precursor, βAPP. Examples of the latter include mydriasis test with cholilytic drug, Apo E and other genes relating to Alzheimer's disease. However, no good results are obtained.

Serine proteases are also considered to play important role in cancer cells. The reason why extermination of cancer by surgical treatment or topical irradiation of radioactive ray is difficult is metastasis capability of cancer. For spread of solid tumor cells in a body, they should loosen their adhesion to original adjacent cells, followed by separating from an original tissue, passing through other tissues to reach blood vessel or lymph node, entering into the circulatory system through stratum basal and endothelial layer of the vessel, leave from the circulatory system at somewhere in the body, and surviving and proliferating in a new environment. While adhesion to adjacent epidermal cells is lost when expression of cadherin which is an intercellular adhesive molecule of epithelium is stopped, to break through tissues is considered to depend on proteolytic enzymes which decompose an extracellular matrix.

As enzymes which decompose the matrix, mainly, metal proteases (Rha, S. Y. et al., Breast Cancer Research Treatment, 43, 175, 1997) and serine proteases are known. They cooperate to decompose matrix protein such as collagen, laminin and fibronectin. Among serine proteases known to be concerned in decomposition of the matrix, in particular, there is urokinase type plasminogen activator (U-PA). U-PA has a role as a trigger specific for a protein decomposition chain reaction. Its direct target is plasminogen. It is present in blood abundantly and is a precursor of an inactive serine protease which accumulates in reconstructed sites of tissues such as injured sites and tumors as well as inflammatory sites. In addition, as proteases which are concerned in metastasis and infiltration of cancers, for example, a tissue factor, lysosomal type hydrolase and collagenase have been known.

At present, cancer is the top cause of death in Japan and more than 200,000 people are died per year. Then, specific substances which can be used as markers for diagnosis and therapy or prophylaxis of cancer are studied intensively. Such specific substances are referred to as tumor markers or tumor marker relating biomarkers. They are utilized in aid of diagnosis before treatment of cancer, for presuming carcinogenic organ and pathological tissue type, for monitoring effect of treatment, for finding recurrence early, for presuming prognosis, and the like. At present, tumor markers are essential in clinical analyses. Among them, alpha fetoprotein (AFP) which has high specificity to hepatocellular carcinoma and yolk sac tumor (Taketa K. et al., Tumour Biol., 9, 110, 1988), and carcinoembronic antigen (CEA) are used worldwide. In the future, tumor markers will be required more and more, and it is desired to develop, for example, organ specific markers and tumor cell specific markers which are highly reliable serologic diagnosis of cancer. Up to now, humunglandular kallikrein (hK2) which is a serine protease expressed at human prostatic epithelial cells has been reported as a marker for prostatic cancer. And, hK2 has 78% homology with the sequence of prostatic specific antigen (PSA) and PSA is also used widely as a biochemical marker of prostatic cancer (Mikolajczyk, S. d. et al., Prostate, 34, 44, 1998; Pannek, J. et al., Oncology, 11, 1273, 1997; Chu, T. M. et al., Tumour Biology, 18, 123, 1997; Hsieh, M. et al., Cancer Res., 57, 2651, 1997). Moreover, CYFRA (CYFRA 21-1) for measuring cytokeratin 19 fragment in serum is reported to be useful for lung cancer (Sugiyama, Y. et al., Japan J. Cancer Res., 85, 1178, 1994). Gastrin release peptide precursor (ProGRP) is reported to be useful as a tumor marker (Yamaguchi, K. et al., Japan, J. Cancer Res., 86, 698, 1995).

OBJECTS OF THE INVENTION

Thus, the main object of the present invention is to provide a novel serine protease which can be used for treating or diagnosing various diseases such as Alzheimer's disease (AD), epilepsy, cancer, inflammation, sterility, prostate hypertropy and the like in various tissues such as each part of brain, medulla, prostate, testicle, mucous membrane gland, placenta, heart, lung and the like, and can be used as an excellent marker instead of that presently used.

SUMMARY OF THE INVENTION

Under these circumstances, the present inventors have succeeded in cloning of cDNA encoding novel human and mouse serine proteases. The present inventors have shown that the mature type of the novel human serine protease (hBSSP6) is composed of 229 amino acids, the prostate type thereof is composed of 282 amino acids (the −53rd to 229th amino acids of SEQ ID NO: 2) and the brain type thereof is composed of 250 amino acids (the −21st to 229th amino acids of SEQ ID NO: 2). The placenta type thereof is considered to be a larger protein started from methionine located at a more upstream region. Further, the present inventors have shown that the mature type of mutant type of hBSSP6 (hereinafter referred to as mutant hBSSP6) is composed of 254 amino acids (the 1st to 254 amino acids of SEQ ID NO: 6). The present inventors have shown that the mature type of the novel mouse serine protease (mBSSP6) is composed of 229 amino acids (the 1st to 229th amino acids of SEQ ID NO: 4), the brain type thereof is composed of 249 amino acids (the −20th to 229th amino acids of SEQ ID NO: 4) and the prostate type thereof is composed of 276 amino acids (the −47th to 229th amino acids of SEQ ID NO: 4). In addition, amino acid sequences of the mature type serine proteases contain consensus sequences having serine protease activity.

In summary, the 1st feature of the present invention is amino acid sequences of biological active mature serine proteases hBSSP6 and mBSSP6 and nucleotide sequences encoding the amino acid sequences.

That is, they are the amino acid sequence composed of 229 amino acids (the 1st to 229th amino acids) represented by SEQ ID NO: 2 (the mature type hBSSP6 (SEQ ID NO: 6)) and a nucleotide sequence encoding the amino acid sequence (the 272nd to 958th bases of SEQ ID NO: 1). Further, they are the amino acid sequence composed of 254 amino acids (the 1st to 254 amino acids) represented by SEQ ID NO: 6 (the mutant hBSSP6 (SEQ ID NO: 6)) and a nucleotide sequence encoding the amino acid sequence (the 114th to 875th bases of SEQ ID NO: 5). In addition, they include amino acid sequences substantially similar to SEQ ID NOS: 2 and 6 and nucleotide sequences encoding such similar amino acid sequences. Further, they include modified derivatives of proteins having these amino acid sequences. An amino acid sequence substantially similar to a given amino acid sequence used herein means an amino acid sequence derived from the given amino acid sequence by modification such as substitution, deletion, addition and/or insertion of one to several amino acids with maintaining the same property as that of the protein having the given amino acid sequence. The modified derivative of the proteins includes, for example, phosphate adduct, sugar chain adduct, metal adduct (e.g., calcium adduct), the protein fused to another protein such as albumin etc., dimer of the protein, and the like.

Further, they are the amino acid sequence composed of 229 amino acids (the 1st to 229th amino acids) or SEQ ID NO: 4 (the mature type mBSSP6 (SEQ ID NO: 4)) and a nucleotide sequence encoding the amino acid sequence (the 224th to 930th bases of SEQ ID NO: 3). In addition, they include amino acid sequences substantially similar to the amino acid sequence and nucleotide sequences encoding such similar amino acid sequences. Further, they include modified derivatives of proteins having these amino acid sequences.

The 2nd feature of the present invention is an amino acid sequence composed of 282 amino acids (prostate type hBSSP6 (the −53rd to 229th amino acids of SEQ ID NO: 2)) wherein 53 amino acids represented by the −53rd to −1st amino acids of SEQ ID NO: 2 is added to the N-terminus side of the mature type hBSSP6 amino acid sequence (SEQ ID NO: 2) and a nucleotide sequence encoding the amino acid sequence (the 113th to 958th bases of SEQ ID NO: 1). In addition, this feature includes amino acid sequences substantially similar to the amino acid sequence and nucleotide sequences encoding these substantially similar amino acid sequences. Further, this feature includes modified derivatives of proteins having these amino acid sequences.

The 3rd feature of the present invention is an amino acid sequence composed of 250 amino acids (the brain type hBSSP6 (the −21st to 229th amino acids of SEQ ID NO: 2)) wherein 21 amino acids represented by the −21st to −1st amino acids of SEQ ID NO: 2 is added to the N-terminus side of the mature type hBSSP6 amino acid sequence (SEQ ID NO: 2) and a nucleotide sequence encoding the amino acid sequence (the 209th to 958th bases of SEQ ID NO: 1). In addition, this feature includes amino acid sequences substantially similar to the amino acid sequence and nucleotide sequences encoding these substantially similar amino acid sequences. Further, this feature includes modified derivatives of proteins having these amino acid sequences.

The 4th feature of the present invention is an amino acid sequence composed of 249 amino acids (the brain type mBSSP6 (the −20th to 229th amino acids of SEQ ID NO: 4)) wherein 20 amino acids represented by the −21st to −1st amino acids of SEQ ID NO: 4 is added to the N-terminus side of the mature type mBSSP6 amino acid sequence (SEQ ID NO: 4) and a nucleotide sequence encoding the amino acid sequence (the 184th to 930th bases of SEQ ID NO: 1). In addition, this feature includes amino acid sequences substantially similar to the amino acid sequence and nucleotide sequences encoding these substantially similar amino acid sequences. Further, this feature includes modified derivatives of proteins having these amino acid sequences.

The 5th feature of the present invention is an amino acid sequence composed of 276 amino acids (the prostate type mBSSP6 (the −47th to 229th amino acids of SEQ ID NO: 4)) wherein 47 amino acids represented by the −47th to −1st amino acids of SEQ ID NO: 4 is added to the N-terminus side of the mature type mBSSP6 amino acid sequence (SEQ ID NO: 4) and a nucleotide sequence encoding the amino acid sequence (the 103rd to 930th bases of SEQ ID NO: 3). In addition, this feature includes amino acid sequences substantially similar to the amino acid sequence and nucleotide sequences encoding these substantially similar amino acid sequences. Further, this feature includes modified derivatives of proteins having these amino acid sequences.

The 6th feature of the present invention is an amino acid sequence composed of 275 amino acids (the mutant hBSSP6 (the −21st to 254th amino acids of SEQ ID NO:6)) wherein 21 amino acids represented by the −21st to −1st amino acids of SEQ ID NO:6 is added to the N-terminus side of the mature type of mutant hBSSP6 amino acid sequence (the 1st to 254th amino acids of SEQ ID NO:6) and a nucleotide sequence encoding the amino acid sequence (the 51st to 875th of SEQ ID NO:5). In addition, this feature includes amino acid sequences substantially similar to the amino acid sequence and nucleotide sequences encoding these substantially similar amino acid sequences. Further, this feature includes modified derivatives of proteins having these amino acid sequences.

The 7th feature of the present invention is a vector comprising the nucleotide sequence according to any of the above 1st to the 6th features, and transformant cells transformed with the vector.

The 8th feature of the present invention is a process for producing BSSP6 protein from the transformed cells of the 7th feature.

The 9th feature of the present invention is a transgenic non-human animal, wherein the expression level of BSSP6 gene has been altered.

The 10th feature of the present invention is an antibody against BSSP6 protein or its fragment and a process for producing thereof.

The 11th feature of the present invention is a method for determining BSSP6 protein or its fragment in a specimen using the antibody of the 9th feature.

The 12th feature of the present invention is a diagnostic marker of diseases comprising BSSP6 protein.

Hereinafter, unless otherwise stated, the nucleotide sequence represented by each SEQ ID NO: includes the above-described various fragments thereof, and similar nucleotide sequences and their fragments. Likewise, the amino acid sequence represented by each SEQ ID NO: includes the above-described various fragments thereof, similar amino acid sequences and their fragments, and modified derivatives thereof. In addition, unless otherwise stated, BSSP6, hBSSP6 (including the mutant hBSSP6), and mBSSP6 include proteins having the above-described respective amino acid sequences.

DETAILED DESCRIPTION OF THE INVENTION

Figure 1:
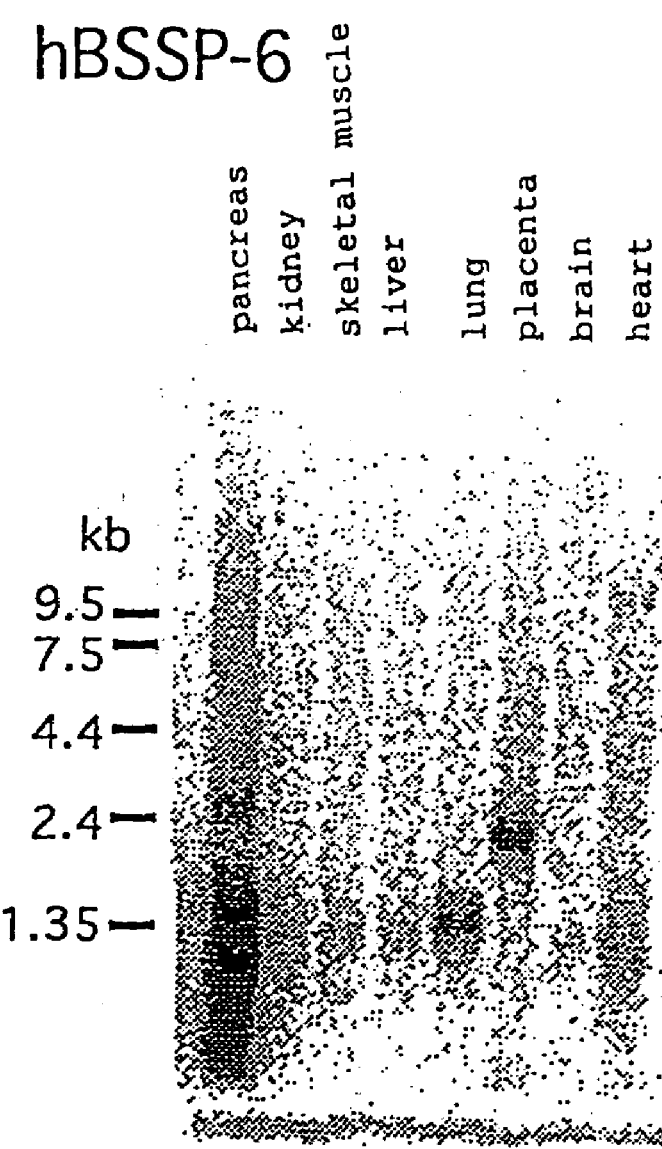
FIG. 1 illustrates the results of northern blotting using human multiple tissue blot membrane.

The term "pro part" used herein means a part of a pro-form, i.e., the pro-form from which the corresponding active type protein part is removed. The term "pre part" used herein means a part of a prepro-form, i.e., the prepro-form from which the corresponding pro-form is removed. The term "prepro part" used herein means a part of a prepro-form, i.e., the prepro-form from which the corresponding active type protein part is removed.

The amino acid sequence represented by SEQ ID NO: 2 (the 1st to 229th amino acids) is the hBSSP6 mature or active type protein composed of 229 amino acids, and the nucleotide sequence encoding the amino acid sequence is composed of 687 bases. The present inventors have shown that the serine protease activity is maintained even when one to several amino acids of the N-terminus in the amino acid sequence of the mature type protein of the present invention is deleted or added, while the above amino acid sequence is preferred.

The amino acid sequence represented by SEQ ID NO: 2 (the −70th to 229th amino acids) is the hBSSP6 prostate type protein composed of 299 amino acids, and the nucleotide sequence encoding the amino acid sequence is composed of 897 bases. The present inventors have shown that the serine protease activity is maintained even when one to several amino acids of the N-terminus in the amino acid sequence of the prostate type protein is deleted or added, while the above amino acid sequence is preferred. The −70th to −1st amino acids is the prepro or pro part and this is considered to be a precursor type of hBSSP6 protein.

The amino acid sequence represented by SEQ ID NO: 2 (the −21st to 229th amino acids) is the hBSSP6 brain type protein composed of 250 amino acids, and the nucleotide sequence encoding the amino acid sequence is composed of 750 bases. The present inventors have shown that the serine protease activity is maintained even when one to several amino acids of the N-terminus in the amino acid sequence of the brain type protein is deleted or added, while the above amino acid sequence is preferred. The −21st to −1st amino acids is the prepro or pro part and this is considered to be a precursor type of hBSSP6 protein.

The amino acid sequence represented by SEQ ID NO: 4 (the 1st to 229th amino acids) is the mBSSP6 mature or active type protein composed of 229 amino acids, and the nucleotide sequence encoding the amino acid sequence is composed of 687 bases. The present inventors have shown that the serine protease activity is maintained even when one to several amino acids of the N-terminus in the amino acid sequence of the mature type protein is deleted or added, while the above amino acid sequence is preferred.

The amino acid sequence represented by SEQ ID NO: 4 (the −20th to 229th amino acids) is the mBSSP6 brain type protein composed of 249 amino acids, and the nucleotide sequence encoding the amino acid sequence is composed of 747 bases. The present inventors have shown that the serine protease activity is maintained even when one to several amino acids of the N-terminus in the amino acid sequence of the brain type protein is deleted or added, while the above amino acid sequence is preferred. The −20th to −1st amino acids is the prepro or pro part and this is considered to be a precursor type of mBSSP6 protein.

The amino acid sequence represented by SEQ ID NO: 4 (the −47th to 229th amino acids) is the mBSSP6 prostate type protein composed of 276 amino acids, and the nucleotide sequence encoding the amino acid sequence is composed of 828 bases. The present inventors have shown that the serine protease activity is maintained even when one to several amino acids of the N-terminus in the amino acid sequence of the prostate type protein is deleted or added, while the above amino acid sequence is preferred. The −47th to −1st amino acids is the prepro or pro part and this is considered to be a precursor type of mBSSP6 protein.

The amino acid sequence represented by SEQ ID NO: 6 (the 1st to 254th amino acids) is the mutant hBSSP6 mature or active type protein composed of 254 amino acids, and the nucleotide sequence encoding the amino acid sequence is composed of 762 bases. The amino acid sequence of the mutant hBSSP6 differs from that of hBSSP6 in that the amino acid sequence of hBSSP6 (SEQ ID NO: 2) corresponds to that of mutant hBSSP6 (SEQ ID NO: 6) from which the 46th to 70th amino acids thereof is removed. The term "mutant" of mutant hBSSP6 is used to merely differentiate it from hBSSP6.

The amino acid sequence represented by SEQ ID NO: 6 (the −21st to 254th amino acids) is a precursor protein of the mutant hBSSP6 composed of 275 amino acids, and the nucleotide sequence encoding the amino acid sequence is composed of 825 bases. The −21st to −1st amino acids is the prepro or pro part.

The nucleotide sequences encoding hBSSP6 (including mutant hBSSP6, hereinafter simply referred to as hBSSP6) or mBSSP6 of the present invention can be obtained by preparing mRNAs from cells expressing the protein and converting it into double stranded DNAs according to a conventional manner. For preparing mRNA, guanidine isothiocyanate-calcium chloride method (Chirwin, et al., Biochemistry, 18, 5294, 1979) or the like can be used. For preparing poly (A)+RNA from total RNAs, there can be used affinity chromatography using a carrier, for example, Sepharose, latex particles, etc., to which oligo (dT) is attached, and the like. The above-obtained RNA can be used as a template and treated with reverse transcriptase by using, as a primer, oligo (dT) which is complementary to the poly (A) strand at the 3'-terminus, or a random primer, or a synthesized oligonucleotide corresponding to a part of the amino acid sequence of hBSSP6 or mBSSP6 to obtain a hybrid MRNA strand comprising DNA complementary to the mRNA or cDNA. The double stranded DNA can be obtained by treating the above-obtained hybrid mRNA strand with E. coli RNase, E. coli DNA polymerase and E. coli DNA ligase to convert into a DNA strand.

It is also possible to carry out cloning by RT-PCR method using primers synthesized on the basis of the nucleotide sequence of hBSSP6 or mBSSP6 gene and using hBSSP6 or mBSSP6 expressing cell poly (A)+RNA as a template. Alternatively, the desired cDNA can be obtained without using PCR by preparing or synthesizing a probe on the basis of the nucleotide sequence of hBSSP6 or mBSSP6 gene and screening a cDNA library directly. Among genes obtained by these methods, the gene of the present invention can be selected by confirming a nucleotide sequence thereof. The gene of the present invention can also be prepared according to a conventional method using chemical syntheses of nucleic acids, for example, phosphoamidite method (Mattencci, M. D. et al., J. Am. Chem. Soc., 130, 3185, 1981) and the like.

By using the thus-obtained hBSSP6 or mBSSP6 gene, their expression in various tissues can be examined.

In case of northern blotting analysis, the expression of hBSSP6 is observed in each part of brain, medulla, placenta, lung, heart, prostate, testicle, mucous membrane gland, etc., and the expression of mBSSP6 is observed in brain of 15-day fetus and testicle and prostate of 3-month-old mouse. In case of RT-PCR analysis, the expression of hBSSP6 is observed in hippocampus and prostate of the adults, and the expression of mBSSP6 is observed in brain of newborn to 12-day-old mice and in prostate of 4-month-old mouse. mRNA of the mutant hBSSP6 is expressed in prostatic cancer cell strains, PC3, DU145 and LNCaP. As for tissues, it is expressed in testicle, lung, fetus brain, and adult hippocampus. Then, the novel proteases of the present invention are presumed to play various roles in brain, prostate, medulla, lung, placenta, heart, testicle and mucous membrane gland. For example, in brain, there is a possibility that they can be used for treatment and diagnosis of brain diseases such as Alzheimer's disease (AD), epilepsy, brain tumor and the like. Further, in other tissues, there is a possibility that they can be used for treatment and diagnosis of various diseases such as cancer, in particular, prostatic cancer, inflammation, sterility, prostate hypertrophy and the like. Further, it is presumed they may have a certain influence on blood coagulation, fibrinolysis and complement systems.

In general, many genes of eucaryote exhibit polymorphism and, sometimes, one or more amino acids are substituted by this phenomenon. Further, even in such case, sometimes, a protein maintains its activity. Then, the present invention includes a gene encoding a protein obtained by modifying a gene encoding the amino acid sequence represented by SEQ ID NO: 2, 4 or 6, artificially, in so far as the protein has the characteristic function of the gene of the present invention. Further, the present invention includes a protein which is a modification of the amino acid sequence represented by SEQ ID NO: 2, 4 or 6 in so far as the protein has the characteristics of the present invention. Modification is understood to include substitution, deletion, addition and/or insertion. In particular, the present inventors have shown that, even when several amino acids are added to or deleted from the N-terminus amino acid of hBSSP6 or mBSSP6 mature protein represented by SEQ ID NO: 2 or 4, the resultant sequence maintains its activity.

That is, the present invention includes a protein comprising either amino acid sequence described in SEQ ID NOS: 2. 4 and 6; or one of these amino acid sequences wherein one to several amino acids have been substituted, deleted, added and/or inserted, and being belonging to serine protease family.

Each codon for the desired amino acid itself has been known and it can be selected freely. For example, codons can be determined according to a conventional manner by taking into consideration of frequency of use of codons in a host to be utilized (Grantham, R. et al., Nucleic Acids Res., 9, r43, 1989). Therefore, the present invention also includes a nucleotide sequence appropriately modified by taking into consideration of degeneracy of a codon. Further, these nucleotide sequences can be modified by a site directed mutagenesis using a primer composed of a synthetic oligonucleotide encoding the desired modification (Mark, D. F. et al., Proc. Natl. Acad. Sci. USA., 81, 5662, 1984), or the like.

Furthermore, the DNA of the present invention includes DNA which is hybridizable to either of nucleotide sequences described in SEQ ID NOS: 1, 3 and 5, or nucleotide sequences complementary to these nucleotide sequences in so far as the protein encoded by the nucleotide sequence has the same properties as those of hBSSP6 or mBSSP6 of the present invention. It is considered that many of sequences which are hybridizable to a given sequence under stringent conditions have a similar activity to that of a protein encoded by the given sequence. The stringent conditions according to the present invention includes, for example, incubation in a solution containing 5×SSC, 5% Denhardt's solution (0.1% BSA, 0.1% Ficol 1400, 0.1% PVP), 0.5% SDS and 20 µg/ml denatured salmon sperm DNA at 37° C. overnight, followed by washing with 2×SSC containing 0.1% SDS at room temperature. Instead of SSC, SSPE can be appropriately used.

Probes for detecting a hBSSP6 or mBSSP6 gene can be designed based on either of nucleotide sequences described in SEQ ID NOS: 1, 3 and 5. Or, primers can be designed for amplifying DNA or RNA containing the nucleotide sequence. To design probes or primers is carried out routinely by a person skilled in the art. An oligonucleotide having a designed nucleotide sequence can be synthesized chemically. And, when a suitable label is added to the oligonucleotide, the resultant oligonucleotide can be utilized in various hybridization assays. Or, it can be utilized in nucleic acid synthesis reactions such as PCR. An oligonucleotide to be utilized as a primer has, preferably, at least 10 bases, more preferably 15 to 50 bases in length. An oligonucleotide to be utilized as a probe has, preferably, 100 bases to full length.

Moreover, it is possible to obtain a promoter region and an enhancer region of a hBSSP6 or mBSSP6 gene present in the genome based on the cDNA nucleotide sequence of hBSSP6 or mBSSP6 provided by the present invention. Specifically, these control regions can be obtained according to the same manner as described in JP 6-181767 A; J. Immunol., 155, 2477, 1995; Proc. Natl. Acad. Sci., USA, 92, 3561, 1995 and the like. The promoter region used herein means a DNA region which is present upstream from a transcription initiation site and controls expression of a gene. The enhancer region used herein means a DNA region which is present in an intron, a 5'-non-translated region or a 3'-non-translated region and enhances expression of a gene.

The present invention also relates to a vector comprising the nucleotide sequence represented by SEQ ID NO: 1 or a nucleotide sequence encoding the amino acid sequence represented by SEQ ID NO: 2; the nucleotide sequence represented by SEQ ID NO: 3 or a nucleotide sequence encoding the amino acid sequence represented by SEQ ID NO: 4; the nucleotide sequence represented by SEQ ID NO: 5 or a nucleotide sequence encoding the amino acid sequence represented by SEQ ID NO: 6; or a nucleotide sequence similar to them. A nucleotide sequence similar to a give nucleotide sequence used herein means a nucleotide sequence which is hybridizable to the given nucleotide sequence or its complementary nucleotide sequence under the above-described stringent conditions and encodes a protein having the same properties as those of the protein encoded by the nucleotide sequence.

The vector is not specifically limited in so far as it can express the protein of the present invention. Examples thereof include pBAD/His, pRSETA, pcDNA2.1, pTrcHis2A, pYES2, pBlueBac4.5, pcDNA3.1 and pSecTag2 manufacture by Invitrogen, pET and pBAC manufactured by Novagen, pGEM manufactured by Promega, pBluescriptII manufactured by Stratagene, pGEX and pUC18/19 manufactured by Pharmacia, PfastBAC1 manufactured by GIBCO and the like. Preferably, a protein expression vector (described in the specification of a patent application entitled "Protein expression vector and its use" and filed by the same applicant on the same day) is used. This expression vector is constructed by using pCRII-TOPO vector described in the Examples hereinafter, or a commercially available expression vector, for example pSecTag2A vector or pSecTag2B vector (Invitrogen) and integrating a secretory signal nucleotide sequence suitable for expression of the protein of the present invention, in the 3' downstream side thereof, a Tag nucleotide sequence, a cleavable nucleotide sequence and a cloning site, into which a nucleotide sequence encoding a target protein can be inserted, in this order. More specifically, it is preferred to use trypsin signal as the secretory signal, a nucleotide sequence encoding polyhistidine as the Tag nucleotide sequence, and a nucleotide sequence encoding an amino acid sequence which is susceptible to enzyme-specific cleavage, i.e., a nucleotide sequence encoding the amino acid sequence of Asp-Asp-Asp-Asp-Lys (SEQ ID NO:40) (said amino acid sequence is recognized by enterokinase, and the recombinant fusion protein is cleaved at the C-terminus part thereof) as the cleavable nucleotide sequence.

Furthermore, the present invention provides transformed cells having the nucleotide sequence of the present invention in an expressible state by means of the above vector. Preferably, host cells to be used for the transformed cells of the present invention are animal cells and insect cells. However, host cells include any cells (including those of microorganisms) which can express a nucleotide sequence encoding the desired protein in the expression vector of the present invention and can secrete extracellularly.

The animal cells and insect cells used herein include cells derived from human being and cells derived from fly or silk worm. For example, there are CHO cell, COS cell, BHK cell, Vero cell, myeloma cell, HEK293 cell, HeLa cell, Jurkat cell, mouse L cell, mouse C127 cell, mouse FM3A cell, mouse fibroblast, osteoblast, cartilage cell, S2, Sf9, Sf21, High Five™ (registered trade mark) cell and the like. The microorganisms used herein include *E. coli*, yeast or the like.

The protein of the present invention as such can be expressed as a recombinant fused protein so as to facilitate isolation, purification and recognition. The recombinant fused protein used herein means a protein expressed as an adduct wherein a suitable peptide chain are added to the N-terminus and/or C-terminus of the desired protein expressed by a nucleotide sequence encoding the desired protein. The recombinant protein used herein means that obtained by integrating a nucleotide sequence encoding the desired protein in the expression vector of the present invention and cut off an amino acid sequence which derived from nucleic acids other than those encoding the desired protein from the expressed recombinant fused protein, and is substantially the same as the protein of the present invention.

Introduction of the above vector into host cells can be carried out by, for example, transfection according to lipopolyamine method, DEAE-dextran method, Hanahan method, lipofectin method or calcium phosphate method, microinjection, eletroporation and the like.

As described above, the present invention also relates to a process for producing hBSSP6 or mBSSP6 comprising culturing cells transformed with the above nucleotide sequence of the present invention and collecting the produced hBSSP6 or mBSSP6. The culture of cells and separation and purification of the protein can be carried out by a per se known method.

The present invention also relates to an inhibitor of the novel serine protease of the present invention. Screening of the inhibitor can be carried out according to a per se known method such as comparing the enzyme activity upon bringing into contact with a candidate compound with that without contact with the candidate compound, or the like The present invention relates to a non-human transgenic animal whose expression level of hBSSP6 or mBSSP6 gene has been altered. The hBSSP6 or mBSSP6 gene used herein includes cDNA, genomic DNA or synthetic DNA encoding hBSSP6 or mBSSP6. In addition, expression of a gene includes any steps of transcription and translation. The non-human transgenic animal of the present invention is useful for studies of functions or expression control of hBSSP6 or mBSSP6, elucidation of mechanisms of diseases in which hBSSP6 or mBSSP6 is presumed to be involved, and development of disease model animals for screening and safety test of medicine.

In the present invention, expression of a gene can be modified artificially by mutagenizing at a part of several important sites which control normal gene expression (enhancer, promoter, intron, etc.) such as deletion, substitution, addition and/or insertion to increase or decrease an expression level of the gene in comparison with its inherent expression level. This mutagenesis can be carried out according to a known method to obtain the transgenic animal.

In a narrow sense, the transgenic animal means an animal wherein a foreign gene is artificially introduced into reproductive cells by gene recombinant techniques. In a broad sense, the transgenic animal includes an antisense transgenic animal the function of whose specific gene is inhibited by using antisense RNA, an animal whose specific gene is knocked out by using embryonic stem cells (ES cells), and an animal into which point mutation DNA is introduced, and the transgenic animal means an animal into which a foreign gene is stably introduced into a chromosome at an initial stage of ontogeny and the genetic character can be transmitted to the progeny.

The transgenic animal used herein should be understood in a broad sense and includes any vertebrates other than a human being. The transgenic animal of the present invention is useful for studies of functions or expression control of hBSSP6 or mBSSP6, elucidation of mechanisms of diseases associated with cells expressing in a human being, and development of disease model animals for screening and safety test of medicine.

As a technique for creating the transgenic animal, a gene is introduced into a nucleus in a pronucleus stage of egg cells with a micropipette directly under a phase-contrast microscope (microinjection, U.S. Pat. No. 4,873,191). Further, there are a method using embryonic stem cell (ES cell), and the like. In addition, there are newly developed methods such as a method wherein a gene is introduced into a retroviral vector or adenoviral vector to infect egg cells, a sperm vector method wherein a gene is introduced into egg cells through sperms, and the like.

A sperm vector method is a gene recombinant technique wherein a foreign gene is incorporated into sperm cells by adhesion, electroporation, etc., followed by fertilization of egg cells to introduce the foreign gene into the egg cells (M. Lavitranoet et al., Cell, 57, 717, 1989). Alternatively, an in vivo site specific gene recombinant technique such as that using cre/loxP recombinase system of bacteriophage P1, FLP recombinase system of *Saccharomyces cerevisiae*, etc. can be used. Furthermore, introduction of a transgene of the desired protein into a non-human animal using a retroviral vector has been reported.

For example, a method for creating a transgenic animal by microinjection can be carried out as follows.

First, a transgene primarily composed of a promoter responsible for expression control, a gene encoding a specific protein and a poly A signal is required. It is necessary to confirm expression modes and amounts between respective systems because an expression mode and amount of a specific molecule is influenced by a promoter activity, and transgenic animals differ from each other according to a particular system due to the difference in a copy number of an introduced transgene and a introduction site on a chromosome. An intron sequence which is spliced may be previously introduced before the poly A signal because it has been found that an expression amount varies due to a non-translation region and splicing. Purity of a gene to be used for introduction into fertilized egg cells should be as high as possible. This is of importance. Animals to be used include mice for collecting fertilized eggs (5- to 6-week-old), male mice for mating, false pregnancy female mice, seminiferous tubule-ligated mice, and the like.

For obtaining fertilized egg cells efficiently, ovulation may be induced with gonadotropin or the like. Fertilized egg cells are recovered and a gene in an injection pipette is injected into male pronucleus of the egg cells by microinjection. For returning the injected egg cells to a fallopian tube, an animal (false pregnancy female mouse, etc.) is provided and about 10 to 15 eggs/mouse are transplanted. Then, genomic DNA is extracted from the end part of the tail to confirm whether the transgene is introduced into newborn mouse or not. This confirmation can be carried out by detection of the transgene with southern blot technique or PCR technique, or by positive cloning wherein a marker gene, which is activated only when homologous recombination is caused, has been introduced. Further, transcribed products derived from the transgene are detected by northern blot technique or RT-PCR technique to confirm expression of the transgene. Or, western blotting can be carried out with a specific antibody to a protein.

The knockout mouse of the present invention is treated so that the function of mBSSP6 gene is lost. A knockout mouse means a transgenic mouse any of whose gene is destroyed by homologous recombination technique so that its function is deficient. A knockout mouse can be created by carrying out homologous recombination with ES cells and selecting embryonic stem cells wherein either of allele genes are modified or destroyed. For example, embryonic stem cells whose genes are manipulated at blastocyte or morula stage of fertilized eggs are injected to obtain a chimera mouse wherein cells derived from the embryonic stem cells are mixed with those derived from the embryo. The chimera mouse (chimera means a single individual formed by somatic cells based on two or more fertilized eggs) can be mated with a normal mouse to create a heterozygote mouse wherein all of either of the allele genes have been modified or destroyed. Further, a homozygote mouse can be created by mating heterozygote mice.

Homologous recombination means recombination between two genes whose nucleotide sequences are the same or very similar to each other in terms of gene recombination mechanism. PCR can be employed to select homologous recombinant cells. A PCR reaction can be carried out by using a part of a gene to be inserted and a part of a region where the insertion is expected as primers to find out occurrence of homologous recombination in cells which give an amplification product. Further, for causing homologous recombination in a gene expressed in embryonic stem cells, homologous recombinant cells can readily be selected by using a known method or its modification. For example, cells can be selected by joining a neomycin resistant gene to a gene to be introduced to impart neomycin resistance to cells after introduction.

The present invention also provide an antibody recognizing hBSSP6 or mBSSP6 or a fragment thereof. The antibody of the present invention includes an antibody against a protein having the amino acid sequence described in SEQ ID NO: 2, 4 or 6 or its fragment. An antibody against hBSSP6 or mBSSP6 or a fragment thereof (e.g., polyclonal antibody, monoclonal antibody, peptide antibody) or an antiserum can be produced by using hBSSP6 or mBSSP6 or a fragment thereof, etc. as an antigen according to a per se known process for producing an antibody or an antiserum.

The hBSSP6 or mBSSP6 or a fragment thereof is administered to a site of a warm-blooded animal where an antibody can be produced by administration thereof as such or together with a diluent or carrier. For enhancing the antibody production, upon administration, Freund's complete adjuvant or Freund's incomplete adjuvant may be administrated. Normally, the administration is carried out once every 1 to 6 weeks, 2 to 10 times in all. Examples of the warm-blooded to be used include monkey, rabbit, dog, guinea pig, mouse, rat, sheep, goat, chicken and the like with mouse and rat being preferred. As rats, for example, Wistar and SD rats are preferred. As mice, for example, BALB/c, C57BL/6 and ICR mice are preferred.

For producing monoclonal antibody producer cells, individuals whose antibody titer have been recognized are selected from warm-blooded animals, e.g., a mouse immunized with an antigen. Two to 5 days after the last immunization, the spleen or lymph node of the immunized animal is collected and antibody producer cells contained therein are subjected to cell fusion with myeloma cells to prepare a monoclonal antibody producer hybridoma. The antibody titer in an antiserum can be determined by, for example, reacting the antiserum with a labeled hBSSP6 or mBSSP6 as described hereinafter, followed by measurement of the activity bound to the antibody. The cell fusion can be carried out according to a known method, for example, that described by Koehler and Milstein (Nature, 256, 495, 1975) or its modifications (J. Immunol. Method, 39, 285, 1980; Eur. J. biochem, 118, 437, 1981; Nature, 285, 446, 1980). As a fusion promoting agent, there are polyethylene glycol (PEG), Sendai virus and the like. Preferably, PEG is used.

Further, for improving fusion efficiency, lectin, poly-L-lysine or DMSO can be appropriately added.

Examples of myeloma cells include X-63Ag8, NS-1, P3U1, SP2/0, AP-1 and the like with SP2/0 being preferred. The preferred ratio of the number of the antibody producer cells (spleen cells): the number of myeloma cells are 1:20 to 20: 1. PEG (preferably PEG 1000 to PEG 6000) is added at a concentration of about 10 to 80% and the mixture is incubated at 20 to 40° C., preferably 30 to 37° C. for 1 to 10 minutes to carry out the cell fusion efficiently. Screening of anti-hBSSP6 or mBSSP6 antibody producer hybridomas can be carried out by various methods. For example, a supernatant of a hybridoma culture is added to a solid phase to which hBSSP6 or mBSSP6 antigen is adsorbed directly or together with a carrier (e.g., microplate), followed by addition of an anti-immunoglobulin antibody (in case that the cells used in cell fusion is those of a mouse, anti-mouse immunoglobulin antibody is used) or protein A to detect the anti-hBSSP6 or mBSSP6 monoclonal antibody attached to the solid phase. Or, a supernatant of a hybridoma culture is added to a solid phase to which an anti-immunoglobulin antibody or protein A is adsorbed, followed by addition of hBSSP6 or mBSSP6 labeled with a radioactive substance, an enzyme, etc., to detect the anti-hBSSP6 or mBSSP6 monoclonal antibody attached to the solid phase.

Selection and cloning of the anti-hBSSP6 or mBSSP6 monoclonal antibody can be carried out according to a per se known method or its modification. Normally, a HAT (hypoxanthine, aminopterin, thymidine)-added medium for culturing animal cells is used. Any culture medium can be used for selection, cloning and growing up in so far as the hybridoma can grow. For example, there can be used RPMI culture medium containing 1 to 20%, preferably 10 to 20% fetal bovine serum, or a serum-free medium for culturing hybridomas. Preferably, the culture is carried out at a temperature of about 37° C. Normally, the culture time is 5 days to 3 weeks, preferably 1 weeks to 2 weeks. Normally, the culture is carried out under 5% $CO_2$. The antibody titer of a supernatant of a hybridoma culture can be measured according to the same manner as that of the above-described measurement of anti-BSSP6 antibody titer in an antiserum. That is, examples of the measurement to be used include radioimmunoassay (RIA), enzyme-linked immunosorbent assay (ELISA), FIA (fluorescence immunoassay), plaque assay, agglutination reaction method, and the like. Among them, ELISA as shown blew is preferred.

Screening by ELISA

A protein prepared according to the same operation as that for an immunogen is immobilized on the surface of each well of an ELISA plate. Next, BSA, MSA, OVA, KLH, gelatin, skimmed milk, or the like is immobilized on each well to prevent non-specific adsorption. A supernatant of a hybridoma culture is added to each well and is allowed to stand for a given time so that an immunological reaction proceeds. Each well is washed with a washing solution such as PBS or the like. Preferably, a surfactant is added to this washing solution. An enzyme labeled secondary antibody is added and allowed to stand for a given time. As the enzyme to be used for the label, there can be used β-galactosidase, alkaline phosphatase, peroxidase and the like. After washing each well with the same washing solution, a substrate solution of the labeled enzyme used is added so that an enzymatic reaction proceeds. When the desired antibody is present in the supernatant of a hybridoma culture, the enzymatic reaction proceeds and the color of the substrate solution is changed.

Normally, cloning is carried out by a per se known method such as semi-solid agar method, limiting dilution method and the like. Specifically, after confirming a well in which the desired antibody is produced by the above-described method, cloning is carried out to obtain a single clone. For cloning, it is preferred to employ limiting dilution method wherein hybridoma cells are diluted so that one colony is formed per one well of a culture plate. For cloning by limiting dilution method, feeder cells can be used, or a cell growth factor such as interleukin 6, etc. can be added to improve colony forming capability. In addition, cloning can be carried out by using FACS and single cell manipulation method. The cloned hybridoma is preferably cultured in a serum-free culture medium and an optimal amount of an antibody is added to its supernatant. The single hybridoma thus obtained can be cultured in a large amount by using a flask or a cell culture device, or cultured in the abdominal cavity of an animal (J. Immunol. Meth., 53, 313, 1982) to obtain a monoclonal antibody. When culturing in a flask, there can be used a cell culture medium (e.g., IMDM, DMEM, RPMI1640, etc.) containing 0 to 20% of FCS. When culturing in the abdominal cavity of an animal, the animal to be used is preferably the same species or the same line as that from which the myeloma cells used in the cell fusion are derived, a thymus deficient nude mouse or the like, and the hybridoma is transplanted after administration of a mineral oil such as pristane, etc. After 1 to 2 weeks, myeloma cells are proliferated in the abdominal cavity to obtain ascites containing a monoclonal antibody.

The monoclonal antibody of the present invention which does not cross-react with other proteins can be obtained by selecting a monoclonal antibody which recognizes an epitope specific to hBSSP6 or mBSSP6. In general, an epitope presented by an amino acid sequence composed of at least 3, preferably 7 to 20 successive amino acid residues in an amino acid sequence which constitutes a particular protein is said to be an inherent epitope of the protein. Then, a monoclonal antibody recognizing an epitope constituted by a peptide having an amino acid sequence composed of at least 3 successive amino acid residue selected from the amino acid residues disclosed in either of SEQ ID NOS: 2, 4 and 6 can be said to be the monoclonal antibody specific for hBSSP6 or mBSSP6 of the present invention. An epitope common to BSSP6 family can be selected by selecting an amino acid sequence conservative among the amino acid sequences described in SEQ ID NOS: 2, 4 and 6. Or, in case of a region containing an amino acid sequence specific for each sequence, a monoclonal antibody which can differentiate respective proteins can be selected.

Separation and purification of the anti-hBSSP6 or mBSSP6 monoclonal antibody, like a conventional polyclonal antibody, can be carried out according to the same manner as those of immunoglobulins. As a known purification method, there can be used a technique, for example, salting out, alcohol precipitation, isoelectric precipitation, electrophoresis, ammonium sulfate precipitation, absorption and desorption with an ion exchange material (e.g., DEAE), ultrafiltration, gel filtration, or specific purification by collecting only an antibody with an antibody-binding solid phase or an active adsorber such as protein A or protein G, etc., and dissociating the binding to obtain the antibody. For preventing formation of aggregates during purification or decrease in the antibody titer, for example, human serum albumin is added at a concentration of 0.05 to 2%. Alternatively, amino acids such as glycine, α-alanine, etc., in particular, basic amino acids such as lysine, arginine, histidine, etc., saccharides such as glucose, mannitol, etc., or salts such as sodium chloride, etc. can be added. In case of IgM antibody, since it is very liable to be aggregated, it may be treated with β-propionilactone and acetic anhydride.

The polyclonal antibody of the present invention can be produced according to a per se known method or its modification. For example, an immunogen (protein antigen) per se or a complex thereof with a carrier protein is prepared and, according to the same manner as that in the above monoclonal antibody production, a warm-blooded animal is immunized. A material containing an antibody against the protein of the present invention or its fragment is collected from the immunized animal and the antibody is separated and purified to obtain the desired antibody. As for a complex of an immunogen and a carrier protein for immunizing a warm-blooded animal, the kind of a carrier protein and the mixing ratio of a carrier and a hapten are not specifically limited in so far as an antibody against the hapten immunized by cross-linking with the carrier is efficiently produced. For example, there can be used about 0.1 to 20, preferably about 1 to 5 parts by weight of bovine serum albumin, bovine cycloglobulin, hemocyanin, etc. coupled with one part by weight of a hapten. For coupling a carrier and a hapten, various condensing agents can-be used. Examples thereof include glutaraldehyde, carbodiimide or maleimide active ester, active ester agents having thiol group or dithiopyridyl group, and the like. The condensed product is administered as such or together with a carrier or diluent to a site of a warm-blooded animal where an antibody can be produced. For enhancing the antibody production, upon administration, Freund's complete adjuvant or Freund's incomplete adjuvant may be administered. Normally, the administration is carried out once every 2 to 6 weeks, 3 to 10 times in all. The polyclonal antibody can be collected from blood, ascites, or the like, preferably blood of the immunized animal. The polyclonal antibody titer in an antiserum can be measured according to the same manner as measurement of the above monoclonal antibody titer in the antiserum. Separation and purification of the polyclonal antibody, like the above monoclonal antibody, can be carried out according to the same manner as those of immunoglobulins.

The monoclonal antibody and polyclonal antibody against hBSSP6 or mBSSP6 or a fragment thereof can be utilized for diagnosis and treatment of diseases associated with cells expressing hBSSP6 or mBSSP6. By using these antibodies, hBSSP6 or mBSSP6 or a fragment thereof can be determined based on their immunological binding to hBSSP6 or mBSSP6 or a fragment thereof of the present invention. Specifically, examples of a method for determining hBSSP6 or mBSSP6 or a fragment thereof by using these antibodies include a sandwich method wherein the antibody attached to an insoluble carrier and the labeled antibody are reacted with hBSSP6 or mBSSP6 or a fragment thereof to form a sandwich complex and the sandwich complex is detected, as well as a competitive method wherein labeled hBSSP6 or mBSSP6, and hBSSP6 or mBSSP6 or a fragment thereof in the specimen are competitively reacted with the antibody and hBSSP6 or mBSSP6 or a fragment thereof in the specimen is determined based on the amount of the labeled antigen reacted with the antibody.

As a sandwich method for determining hBSSP6 or mBSSP6 or a fragment thereof, there can be used two step method, one step method and the like. In two step method, first, the immobilized antibody is reacted with hBSSP6 or mBSSP6 or a fragment thereof and then unreacted materials are completely removed by washing, followed by addition of the labeled antibody to form immobilized antibody-hBSSP6 or mBSSP6-labeled antibody. In one step method, the immobilized antibody, labeled antibody and hBSSP6 or mBSSP6 or a fragment thereof are added at the same time.

Examples of an insoluble carrier used for the determination include synthetic resins such as polystyrene, polyethylene, polypropylene, polyvinyl chloride, polyester, polyacrylate, nylon, polyacetal, fluorine plastic, etc.; polysaccharides such as cellulose, agarose, etc.; glass; metal; and the like. An insoluble carrier may be shaped in various forms, for example, tray, sphere, fiber, rod plate, container, cell, test tube, and the like. The antibody adsorbed by a carrier is stored at a cold place in the presence of an appropriate preservative such as sodium azide or the like.

For immobilization of the antibody, a known chemical bonding method or a physical adsorption can be used. Examples of a chemical bonding method include a method using glutaraldehyde; maleimide method using N-succusinimidyl-4-(N-maleimidomethyl) cyclohexane-1-carboxylate, N-succusinimidyl-2-maleimide acetate or the like; carbodiimide method using 1-ethyl-3-(3-dimethylaminopropyl)carbodiimide hydrochloride; or the like. In addition, there are maleimidobenzoyl-N-hydroxysuccinimide ester method, N-succinimidyl-3-(2-pyridylthio)propionic acid method, bisdiazobenzidine method, and dipalmityllysine method. Or, it is possible to capture a complex formed beforehand by reacting a materiel to be tested with two antibodies, whose epitopes are different, with an immobilized a 3rd antibody against the antibody.

For labeling, it is preferred to use enzyme, fluorescent substance, luminous substance, radioactive substance, metal chelate, or the like. Examples of the enzyme include peroxidase, alkaline phosphatase, β-D-galactosidase, malate dehydrogenase, *Staphylococcus nuclease*, δ-5-steroidisomerase, α-glycerol phosphate dehydrogenase, triose phosphate isomerase, horseradish peroxidase, asparaginase, glucose oxidase, ribonuclease, urease, catalase, glucose-6-phosphate dehydrogenase, glucoamylase, acetylcholinesterase and the like. Examples of the fluorescent substance include fluorescein isothiocyanate, phycobiliprotein, rhodamine, phycoerythrin, phycocyanin, allophycocyanin, o-phthalaldehyde, and the like. Examples of the luminous substance include isoluminol, lucigenin, luminol, aromatic acridinium ester, imidazole, acridinium salt and its modified ester, luciferin, luciferase, aequorin and the like. Examples of the radioactive substance include $^{125}I$, $^{127}I$, $^{131}I$, $^{14}C$, $^{3}H$, $^{32}P$, $^{35}S$ and the like. The labeling material is not limited to them and any material which can be used for immunological determination can be used. Further, a low molecular weight hapten such as biotin, dinitrophenyl, pyridoxal or fluorescamine may be attached to the antibody. Preferably, horseradish peroxidase is used as a labeling enzyme. This enzyme can be reacted with various substrates and can readily be attached to the antibody by periodate method.

When an enzyme is used as a labeling material, a substrate and, if necessary, a coloring enzyme is used for measuring its activity. In case of using peroxidase as the enzyme, $H_2O_2$ is used as a substrate and, as a coloring agent, there can be used 2,2'-azino-di-[3-ethylbenzthiazoline sulfonic acid] ammonium salt (ABTS), 5'-aminosalicylic acid, o-phenylenediamine, 4-aminoantipyrine, 3,3',5,5'-tetramethylbenzidine and the like. In case of using alkaline phosphatase as the enzyme, o-nitorphenylphosphate, p-nitrophenylphosphoric acid, or the like can be used as a substrate. In case of using β-D-galactosidase as the enzyme, fluorescein-d-(β-D-galactopyranoside), 4-methylumbelliphenyl-β-D-galactopyranoside, or the like can be used as a substrate. The present invention also include a kit comprising the above monoclonal antibody, polyclonal antibody and reagents.

As a cross-linking agent, a known cross-linking agent such as N,N'-o-phenylenedimaleimide, 4-(N-maleimidomethyl) cyclohexanoate N-succinimide ester, 6-maleimidohexanoate N-succineimide ester, 4,4'-dithiopyridine or the like can be utilized. The reaction of these cross-linking-agents with enzymes and antibodies can be carried out by a known method according to properties of a particular cross-linking agent. Further, as the antibody, a fragment thereof, for example, Fab', Fab, F(b'2) can be used as the case may be. A labeled enzyme can be obtained by the same treatment regardless of whether the antibody is polyclonal or monoclonal. When the above labeled enzyme obtained by using a cross-linking agent is purified by a known method such as affinity chromatography or the like, a immunoassay system having more higher sensitivity can be obtained. The enzyme labeled and purified antibody is stored at a dark cold place with addition of a stabilizer such as thimerosal, glycerin or after lyophilization.

An objective to be determined is not specifically limited in so far as it is a sample containing hBSSP6 or MBSSP6 or a fragment thereof, or a sample containing a precursor or a fragment thereof and includes body fluids such as plasma, serum, blood, serum, urine, tissue fluid, cerebrospinal fluid and the like.

The following Examples further illustrate the present invention in detail but are not construed to limit the scope thereof.

EXAMPLE 1

Cloning of Novel Serine Proteases

The cloning was carried out by PCR using a human brain cDNA library (Clontech) as the template and nucleotide sequences corresponding to an amino acid sequence common to serine proteases represented by Primer 1: GTG CTC ACN GCN GCB CAY TG (SEQ ID NO: 36)

Primer 2: CCV CTR WSD CCN CCN GGC GA (SEQ ID NO: 37)

as the primers. Namely, 5 µl of the template, 5 µl of 10×ExTaq buffer, 5 µl of dNTP, 10 pmol of each of the above primers and 0.5 µl of ExTaq (TAKARA) were added and the total volume was adjusted to 50 µl with sterilized water. PCR was carried out by repeating a cycle of heating at 94° C. for 0.5 minute, at 55° C. for 0.5 minute and then at 72° C. for 1 minutes, 35 times. The PCR product was mixed with pCR II-TOPO vector attached to TOPO TA cloning kit (Invitrogen) and the mixture was allowed to stand at room temperature for 5 minutes. Then, according to a conventional manner, E. coli Top 10 attached to the kit was transformed and applied to a LB (Amp+) plate (containing 100 µg/ml of ampicillin). According to a conventional manner, a plasmid was extracted from each colony obtained and its nucleotide sequence was determined by cycle sequencing method with a fluorescence sequencer (ABI). Homology of the sequence of each clone was examined by means of GenBank. Regarding an unknown sequence, i.e., BSSP6 gene, the full length cDNA was obtained by 5' RACE and 3' RACE and, according to the same manner as described above, the nucleotide sequence was determined. Namely, BSSP6 clone specific primers, GSP1 primers (hBSSP6F1 (SEQ ID NO: 18) or hBSSP6R2 (SEQ ID NO: 24)) and GSP2 primers (hBSSP6F2 (SEQ ID NO: 19) or hBSSP6R1 (SEQ ID NO: 23)) were prepared. PCR was carried out by using human brain Marathon-Ready cDNA (Clontech) and human prostate Marathon-Ready CDNA (Clontech), AP1 primer attached to this reagent and either of the above GSP1 primer and heating at 94° C. for 2 minutes once and repeating a cycle of heating at 94° C. for 30 seconds, at 60° C. for 30 seconds and then at 72° C. for 30 seconds 35 times. Then, 5 µl of the PCR product diluted to 1/100, 5 µl of 10×buffer, 5 µl of DNTP, 10 pmol of either of 10 µM of the above GSP2 primer, 10 pmol of AP2 primer attached to the above reagent and 0.5 unit of ExTaq were admixed and adjusted to 50 µl with sterilized water. Then, according to the same manner as the above, PCR was carried out. The PCR product was cloned by the above TOPO TA cloning kit and sequenced to obtain the upstream and downstream regions of the above clone. At this time, as for a clone which did not seem not to cover the full length of the protein, specific primers were prepared based on the newly founded sequence. Further, based on this sequence, the primers capable of amplifying ORF shown in Table 1 (for amplifying each mRNA of brain and prostate (pros.) hBSSP6, different Forward primers were designed) were prepared and PCR carried out using human brain Marathon-ready cDNA and human prostate Marathon-ready cDNA as a template to confirm that these clones were identical. This was cloned into pCR II-TOPO vector attached to TOPO TA cloning kit to obtain the plasmid pCR II/hBSSP6 containing the full length cDNA clone. According to the same manner, the plasmid pCRII/mBSSP6 containing a mouse homologous gene was obtained by carrying out 5' RACE and 3' RACE, followed by cloning. The nucleotide sequences of cDNA encoding hBSSP6 and mBSSP6 are shown in SEQ ID NOS: 1 and 3 and the amino acid sequence of hBSSP6 and mBSSP6 proteins deduced from these nucleotide sequences are shown in SEQ ID NOS: 2 and 4.

TABLE 1

| SEQ ID NO: | Name of primer | Direction | Sequence | Use |
|---|---|---|---|---|
| | | | human BSSP6 | |
| 18 | hBSSP6F1 | Forward | TCAAGCCCCGCTACATAGTT | RACE |
| 19 | hBSSP6F2 | Forward | ATCATGCTGGTGAAGATGGC | RACE |
| 20 | hBSSP6F3 | Forward | GGACTCAAGAGAGGAACCTG | FL* (brain) |
| 21 | hBSSP6F4 | Forward | ATCATCAAGGGGTTCGAGTG | mature |
| 22 | hBSSP6F5 | Forward | CTGCCTTGCTCCACACCTGG | FL* (pros.) |

TABLE 1-continued

| SEQ ID NO: | Name of primer | Direction | Sequence | Use |
|---|---|---|---|---|
| 23 | hBSSP6R1 | Reverse | TTCTCACACTTCTGGTGCTC | RACE |
| 24 | hBSSP6R2 | Reverse | ATGGTGTCTGTGATGTTGCC | RACE |
| 25 | hBSSP6R3/P | Reverse | AACTGCAGGAACCAAACACCAAGTGG | FL* |
| | mouse BSSP6 | | | |
| 26 | mBSSP6F1 | Forward | CGACTTCAACAACAGCCTCC | RACE |
| 27 | mBSSP6F2 | Forward | CTTCTTTACCCGAGCTGTGC | RACE |
| 28 | mBSSP6F3 | Forward | TAAGCTAGGAGAACTGAGGC | FL* (pros.) |
| 29 | mBSSP6F4 | Forward | ATCAAGGGTTATGAGTGC | mature |
| 30 | mBSSP6F5 | Forward | CTTACAGGCTTGGGGATTG | FL* (brain) |
| 31 | mBSSP6R1 | Reverse | GATGATGCCTTGAAGAGATC | RACE |
| 32 | mBSSP6R2 | Reverse | CATGGTGTCTGTGATGTTGCC | RACE |
| 33 | mBSSP6R3/E | Reverse | CGGAATTCGCATTAAGAAGAGGTTGGAG | FL* |

*for full length

EXAMPLE 2

Expression of hBSSP6 or mBSSP6 Gene in Human Beings or Mice Internal Organs

Figure 2:
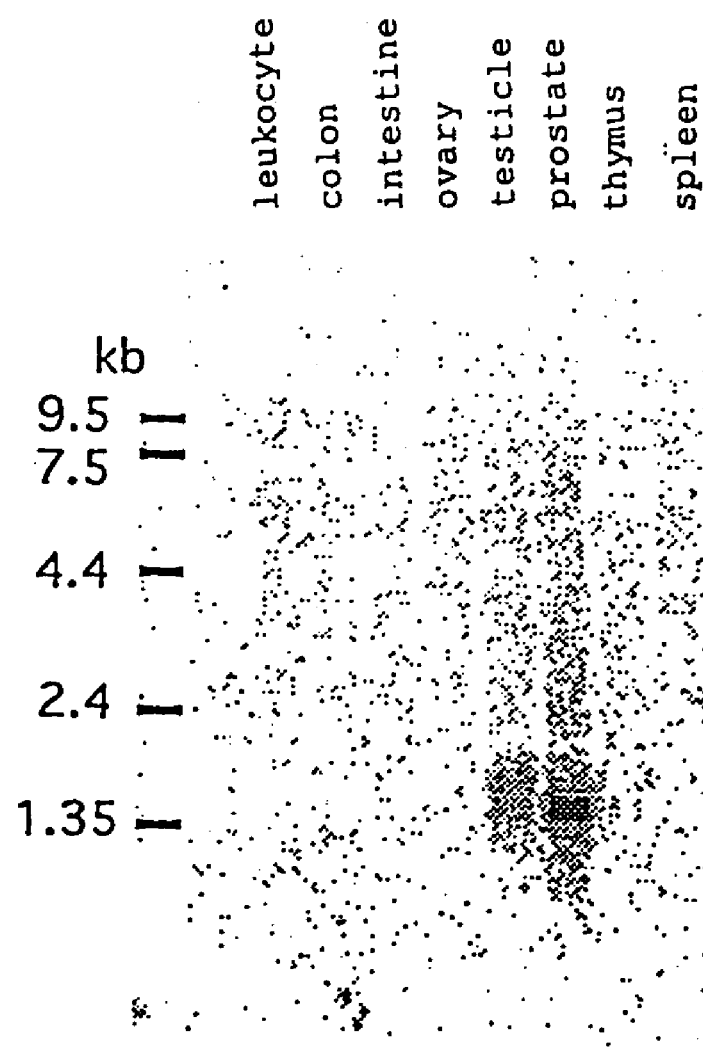
FIG. 2 illustrates the results of northern blotting using human multiple tissue blot II.
Figure 3:
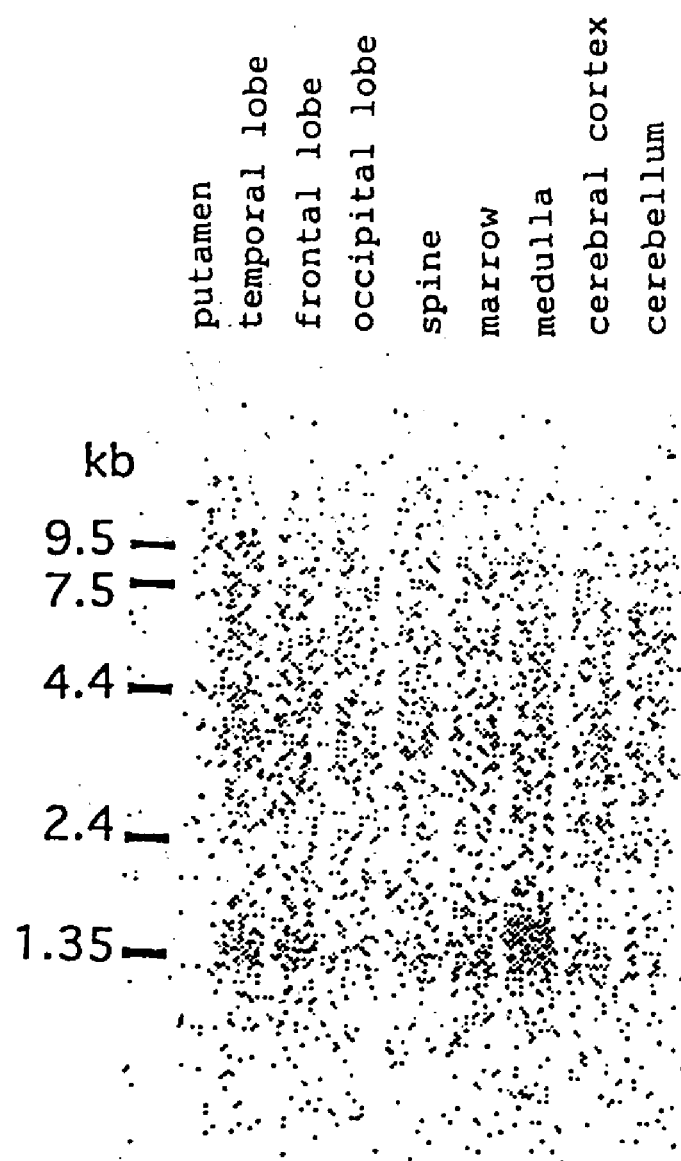
FIG. 3 illustrates the results of northern blotting using human brain multiple tissue blot II.
Figure 4:
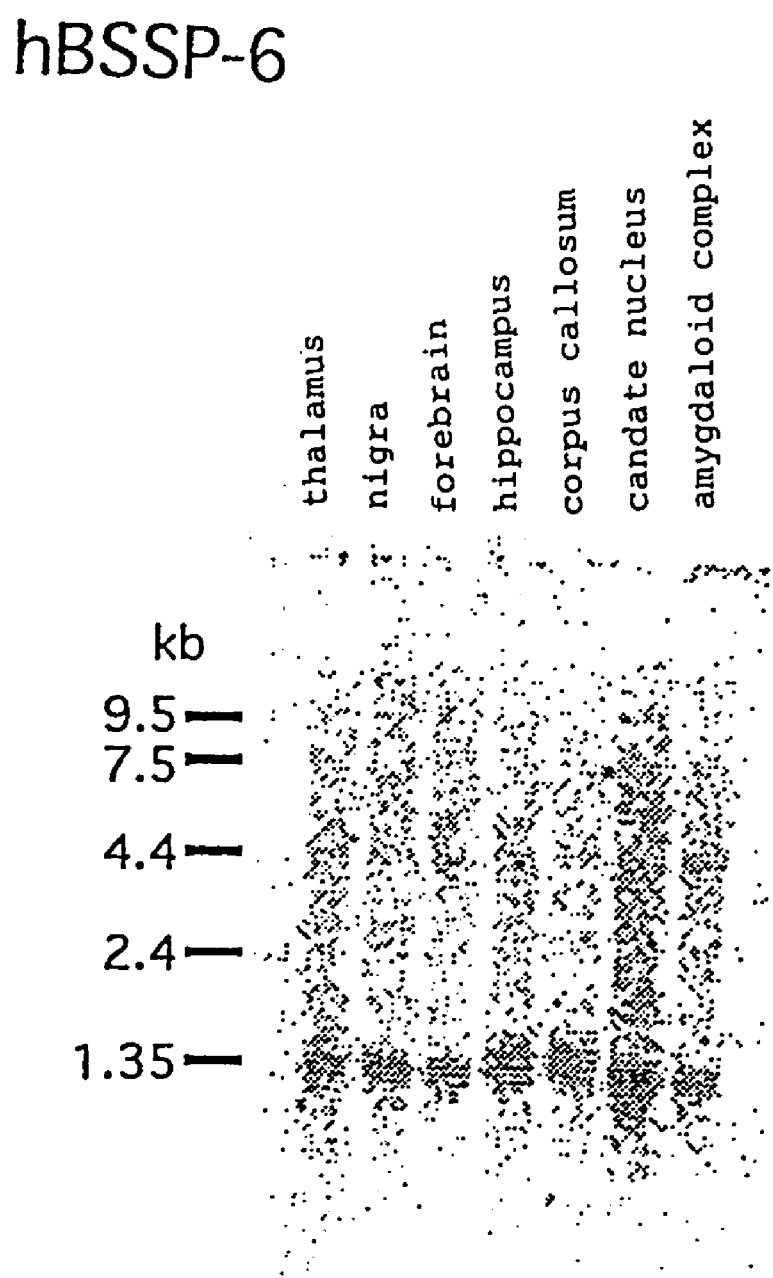
FIG. 4 illustrates the results of northern blotting using human brain multiple tissue blot IV.
Figure 5:
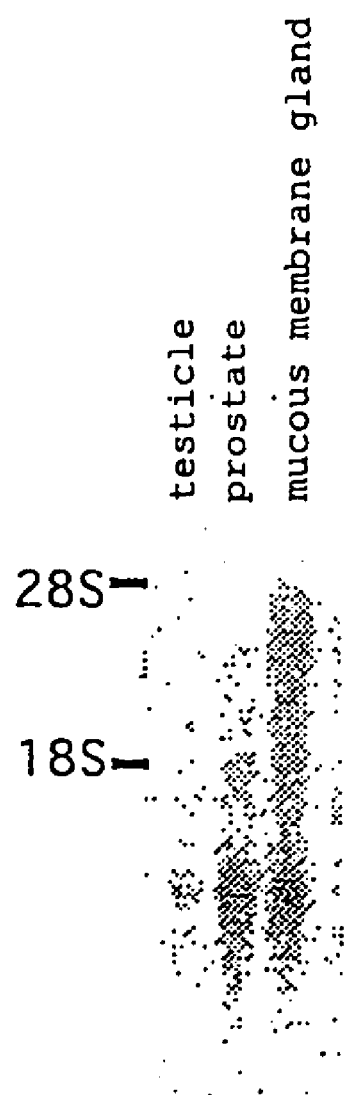
FIG. 5 illustrates the results of northern blotting using mRNA prepared in Example 2 hereinafter.
Figure 6:
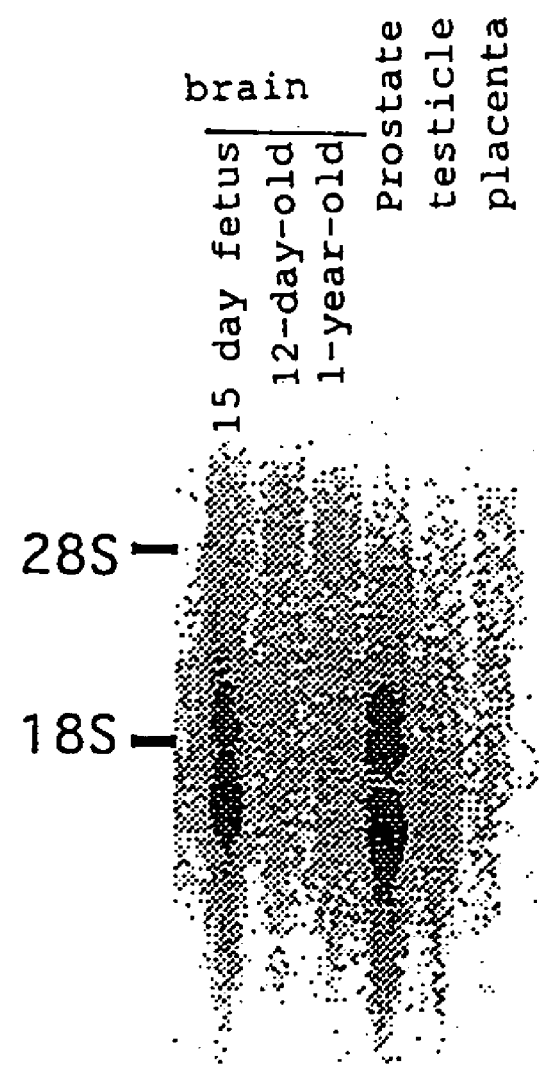
FIG. 6 illustrates the results of northern blotting using mRNA prepared in Example 2 hereinafter.

According to the protocol of QuickPrep Micro mRNA purification Kit (Amersham-Pharmacia), mRNAs were isolated from various internal organs of Balb/c mice or their fetuses and various tissues of human beings. They were subjected to electrophoresis according to a conventional manner and transcribed to a nylon membrane. A probe was prepared separately by isolating a part of a nucleotide sequence encoding the mature protein of mBSSP6 (the 244th to 930th bases of SEQ ID NO: 3) or the mature protein of hBSSP6 (the 272nd to 958th based of SEQ ID NO: 1) from pCR II/mBSSP6 or pCR II/hBSSP6, purifying it and labeling it with $\alpha$-$^{32}$P dCTP. The probe was diluted with 5×SSC and reacted with the above membrane filter at 65° C. overnight. According to the same manner, a probe was prepared by isolating a part of a nucleotide sequence encoding the mature protein of hBSSP6 from pCR II/hBSSP6, purifying it and labeling it with $\alpha$-$^{32}$P dCTP. The probe was diluted with 5×SSC and reacted with human multiple tissue blot, human multiple blot II, human brain multiple tissue blot II or human brain multiple tissue blot IV (Clontech) membrane at 65° C. overnight. Then, each membrane filter was washed twice each with 2×SSC/0.1% SDS at room temperature for 30 minutes, 1×SSC/0.1% SDS at room temperature for 30 minutes and 0.1×SSC/0.1% SDS at 65° C. for 30 minutes. The filter was exposed to an imaging plate for FLA2000 (Fuji Film) for one day to analyze the expression. The results shown in the drawings are those obtained by using human multiple tissue blot (clontech) membrane (FIG. 1), human multiple tissue blot II (FIG. 2), human brain multiple tissue blot II (FIG. 3), human brain multiple tissue blot IV (FIG. 4), mRNAs prepared from testicle, prostate and mucous gland (FIG. 5) as well as mRNAs prepared from brain of 15-day mouse fetuses and brain of 12-day-old and 1-year-old mouse, and mRNAs prepared from prostate, testicle and placenta of 3-month-old mice (FIG. 6). In addition, the mRNAs prepared above were subjected to RT-PCR of hBSSP6 or mBSSP6 by using Ready To Go RT-PCR Beads (Amersham-Pharmacia) and gene specific primers (SEQ ID NOS: 18 and 25) according to the protocol attached to the kit. As seen form FIGS. 1 to 6, in case of northern blotting analysis, the expression of hBSSP6 was observed in each part of brain, placenta, lung, heart, testicle, prostate, mucous membrane gland and the like, and the expression of mBSSP6 was observed in bran of fetuses, prostate and testicle. Further, in case of RT-PCR, the expression of hBSSP6 was observed in hippocampus and prostate of adults. The expression of mBSSP6 was observed in brain and prostate of fetuses to grown up mice. Then, it is presumed that the novel serine proteases have various roles in placenta, lung, heart, testicle, prostate, mucous membrane gland and brain.

EXAMPLE 3

Expression of Novel Serine Protease Mature Protein Encoded by hBSSP6 or mBSSP6 Gene (1) Construction of Expression Plasmid A cDNA region (human being: the 272nd to 958th bases of SEQ ID NO: 1; mouse: the 244th to 930th bases of SEQ ID NO: 3) encoding the mature protein of hBSSP6 or mBSSP6 protein was amplified by PCR using the plasmid pCR II/hBSSP6 or pCR II/mBSSP6 as a template (the primers used were SEQ ID NOS: 21 and 25 for human being, and SEQ ID NOS: 29 and 33 for mouse). Each PCR product was ligated to pTrc-HisB (Invitrogen) which had been digested with BamHI and blunted with mung bean nuclease according to a conventional method. E. coli JM109 was transformed by the resultant and colonies formed were analyzed by PCR to obtain E. coli containing the desired serine protease expressing plasmid pTricHis/hBSSP6 or pTrcHis/mBSSP6.

The resultant E. coli strains were designated E. coli pTrcHis/hBSSP6 and E. coli pTrcHis/mBSSP6 and deposited at National Institute of Bioscience and Human-Technology (NIBH), Agency of Industrial Science & Technology of 1-1-3 Higashi, Tsukuba-shi, Ibaraki-ken, Japan on Oct. 29, 1998 under the accession numbers of FERM P-17039 and FERM P-17036, respectively.

(2) Expression of Protein by *E. coli* Containing Expression Plasmid

A single colony of *E. coli* having the expression plasmid was inoculated in 10 ml of LB (Amp$^+$) culture medium and incubated at 37° C. overnight. This was inoculated in 250 ml of LB (Amp$^+$) culture medium and incubated at 37° C. When the absorbance at 600 nm became 0.5, 250 µl of 0.1 M IPTG (isopropyl-β-D-(-)-thiogalactopyranoside) was added and the incubation was continued for additional 5 hours. The *E. coli* was centrifuged and suspended in a cell disruption buffer (10 mM phosphate buffer pH 7.5, 1 mM EDTA) and sonicated on ice to disrupt *E. coli*. This was centrifuged at 14,000 r.p.m. at 4° C. for 20 minutes to obtain a precipitate. The precipitate was washed twice with a cell disruption buffer containing 0.5% Triton X-100™ and washed with water to remove Triton X-100™. Then, the resultant mixture was dissolved by soaking in a denaturation buffer containing 8 M urea (8M urea, 50 mM Tris pH8.5, 20 mM ME) at 37° C. for 1 hour. The solution was passed through TALON metal affinity resin (Clontech), washed with the denaturation buffer containing 10 mM imidazole, and then eluted with the denaturation buffer containing 100 mM imidazole to purify the solution. The purified product was dialyzed against PBS for 3 days with exchanging the buffer every other night to obtain the protein hBSSP6-His or mBSSP6-His.

EXAMPLE 4

Expression of Novel Serine Protease Mature Protein Encoded by BSSP6 Gene by Using pFBTrypSigTag/BSSP6 and Determination of Enzyme Activity (1) Construction of pFBTrypSigTag/BSSP6

The sequences represented by SEQ ID NOS: 7 and 8 were subjected to annealing and digested with NheI and BamHI. The resultant fragment was inserted into NheI-BamHI digested pSecTag2A (Invitrogen) to obtain pSecTrypHis. Twenty units of BamHI was added to 5 µg of pSecTrypHis vector and the vector was cleaved at 37° C. over 4 hours. Then, 6 units of mung bean nuclease (TAKARA) was added thereto and reacted at room temperature (25° C.) for 30 minutes to blunt the terminal ends. Further, the 3'-terminus side of the cloning site was cleaved with 20 units of XhoI, 1 unit of bacterial alkaline phosphatase (TAKARA) was added thereto and the reaction was carried out at 65° C. for 30 minutes.

Figure 7:
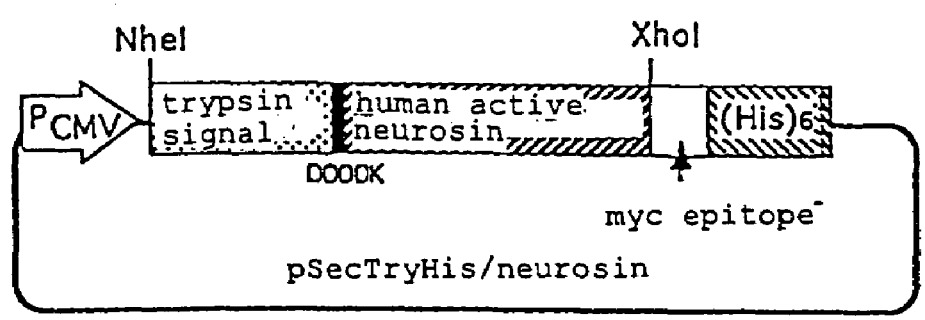
FIG. 7 illustrates the plasmid constructed by the method of Example 4 hereinafter.

According to the same manner as that described in JP 9-149790 A or Biochim. Biophys. Acta, 1350, 11, 1997, mRNA was prepared from COLO201 cells and cDNA was synthesized to obtain the plasmid pSPORT/neurosin. cDNA of an active region of neurosin was obtained from pSPORT/neurosin by PCR using primers having the sequences represented by SEQ ID NOS: 9 and 10. Ten units of XhoI was reacted with the PCR product at 37° C. for 3 hours to cleave XhoI site at the 3'-side thereof. This was inserted into pSecTrypHis by TAKARA ligation kit to obtain pSecTrypHis/neursoin (FIG. 7).

Amplification was carried out by using the primers having the sequences represented by SEQ ID NOS: 11 and 12 so that the peptide of Leu-Val-His-Gly (SEQ ID NO:41) was present at the C-terminus of the part from trypsin signal to the enterokinase recognition site of pSecTrypHis/neurosin. This was inserted between NheI and HindIII sites of pSecTag2A to construct the plasmid pTrypSig.

One µg (0.1 µl) of the plasmid pSecTab2A was treated with the restriction enzymes NheI and BamHI to completely remove a region encoding the leader sequence of IgGk. One hundred pmol portions of DANs represented by SEQ ID NOS: 38 and 39 were added to the resultant solution and the mixture was heated at 70° C. for 10 minutes and subjected to annealing by allowing to stand at room temperature for 30 minutes. Two µl of I solution of DNA ligation kit Ver. 2 (TAKARA) was added to 1 µl portions of His secretory signal sequence and pSecTag2A treated by NheI and BamHI and the reaction was carried out at 16° C. for 30 minutes.

To the reaction mixture was add 0.1 ml of *E. coli* competent cell XL1-Blue (STRATAGENE) and reacted on ice for 30 minutes. Then, the reaction mixture was subjected to heat shock at 42° C. for 60 seconds. After standing on ice for 2 minutes, 0.9 ml of SOC culture medium (Toyo Boseki K.K.) was added thereto and the mixture was shaken with a shaker at 37° C. for 1 hour. The mixture was centrifuged at 5,000 r.p.m. for 1 minutes and the supernatant was discarded. The precipitated competent cells were suspended in the liquid remained in the centrifuge tube and the suspension was applied to 2 ampicillin LB plates containing 100 µg/ml of ampicillin. The plates were incubated at 37° C. overnight. Among the colonies formed, a colony into which DNA of His secretory signal was inserted was selected by PCR to obtain pTrypHis.

Figure 8:
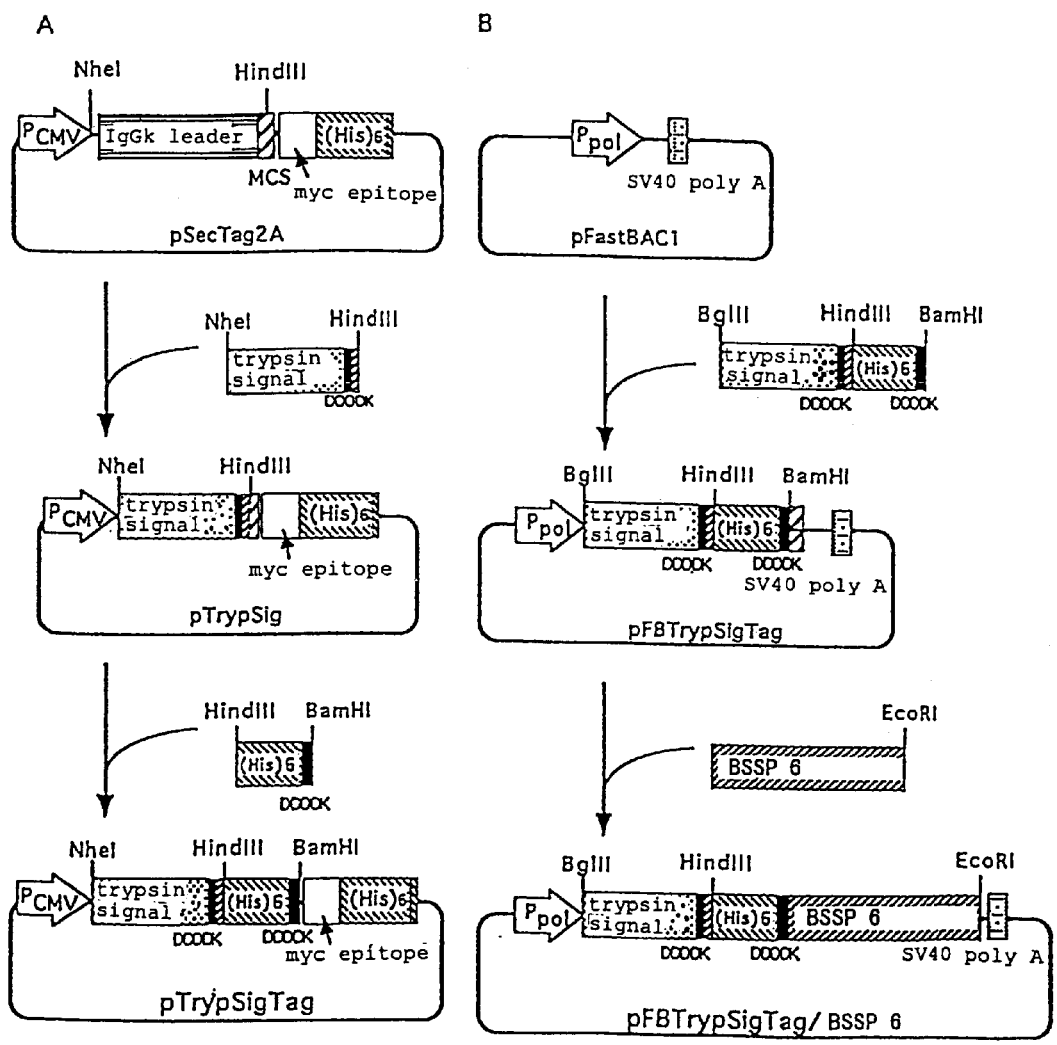
FIG. 8 illustrates the construction of plasmid according to the method of Example 4 hereinafter.

A sequence of about 200 bp containing His Tag region of pTrypHis was amplified by using primers having the sequence represented by SEQ ID NOS: 12 and 13 and a fragment of about 40 bp containing His Tag and enterokinase recognizing site formed by digestion of HindIII and BamHI was inserted into pTrypSig to construct pTrypSigTag (FIG. 8A).

cDNA was prepared by PCR of the sequence from trypsin signal to enterokinase recognizing site of pTrypSigTag using primers having the sequences represented by SEQ ID NOS: 10 and 14 and cut out by digestion with BglII and BamHI. It was inserted into BamHI site of pFastBAC1 (GIBCO). The insertion direction was confirmed by PCR using primers having the sequences represented by SEQ ID NOS 10 and 15. A clone into which the cDNA was inserted in the direction toward transcription and translation by polyhedrin promoter was selected to obtain pFBTrypSigTag.

Twenty units of BamHI was added to 5 µg of pFBTrypSigTag vector and the vector was cleaved at 37° C. over 4 hours, followed by addition of 6 units of mung bean nuclease (TAKARA) and reaction at room temperature (25° C.) for 30 minutes to blunt the terminal ends. Further, the 3'-side of the cloning site was cleaved by 20 units of EcoRI, followed by addition of 1 unit of bacterial alkaline phosphatase (TAKARA). The reaction was carried out at 65° C. for 30 minutes.

cDNA of the active region of hBSSP6 was obtained from pTrcHis/hBSSP6 prepared from *E. coli* pTrcHis/hBSSP6 (accession No. FERM P-17039) or pCRII/hBSSP6 by PCR according to a conventional manner using primers having the sequences of SEQ ID NOS: 16 and 17. The resultant cDNA was inserted into pFBTrypSigTag to obtain pFBTrypSigTag/hBSSP6 (FIG. 7B). At this time, correct insertion of hBSSP6 was confirmed by determining the sequence using a fluorescence-labeled primer having the sequence of SEQ ID NO: 11. cDNA of the active region of mBSSP6 is obtained from pTrcHis/mBSSP6 prepared from *E. coli* pTrcHis/mBSSP6 (FERM P-17036) or pCRII/mBSSP6 obtained in Example 1. According to the same manner as described above, mBSSP6 can be expressed.

Bacmid DNA was transformed with PFBTrypSigTag/ hBSSP6 according to a protocol of Gibco BRL BAC-TO-BAC baculovirus expression system to prepare a recombinant bacmid having chimera hBSSP6 fused with trypsinogen signal peptide, His tag and enterokinase recognizing site. When this was expressed in Sf-9 cell according to a manual of BAC-TO-BAC baculovirus expression system, it was secreted in the culture supernatant from 2 days after infection of the virus.

(2) Determination of Enzyme Activity

Figure 9:
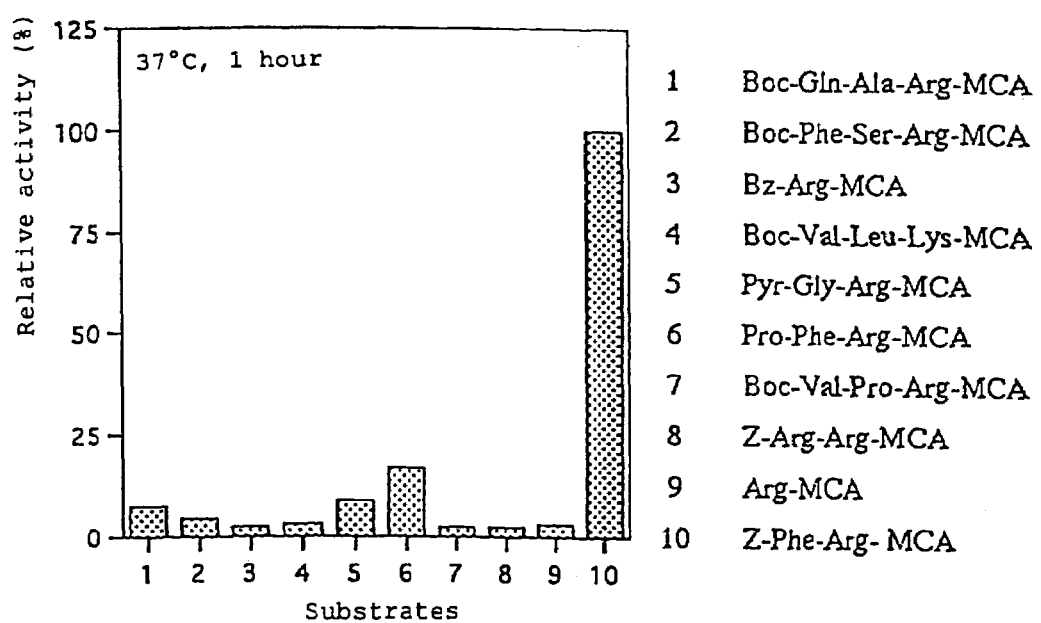
FIG. 9 illustrates the substrate specificity of hBSSP6.

The recombinant fused protein hBSSP6 obtained in the culture supernatant was passed through a chelate column to purify it and, after dialysis, its enzyme activity was determined. First, the culture supernatant was applied to a chelate column (Ni-NTA-Agarose, Qiagen) with PBS buffer and eluted stepwise with a solution of imidazole (Wako Pure Chemical Industries, Ltd.) dissolved in PBS. The resultant imidazole-eluted fraction was applied to a PD-10 column (Pharmacia) to exchange to PBS buffer. Fifty µl of this sample was mixed with 10 µl of enterokinase (1 U/1 µl, Invitrogen) and the reaction was carried out at room temperature for 60 minutes. Each of various synthetic substrates (Peptide Laboratory) was dissolved in DMSO and diluted with 1 M Tris-HCl (pH 8.0) to obtain a substrate solution. Fifty µl of 0.2 M substrate solution was added thereto and further the reaction was carried out at 37° C. After one hour, the fluorescence of AMC (7-amino-4-methylcoumalin) formed by the enzymatic reaction was measured at 380 nm of excitation wavelength and 460 nm of fluorescence wavelength to determine the activity (FIG. 9).

The value shown in the figure is that obtained by subtracting the fluorescence value of enterokinase alone from the measured value.

EXAMPLE 5

Preparation of Anti-hBSSP6 Antibody

An anti-hBSSP6 antibody was prepared as follows.

(1) Immunization

A solution of the recombinant hBSSP6 protein obtained in Example 4 was mixed with Freund's complete adjuvant (DIFCO) in the ratio of 1:1 and the mixture was emulsified. The emulsion was injected subcutaneously to 5 female Balb/c 8-week-old mice so that each mouse received about 100 µg of the recombinant hBSSP6 protein. Then, booster immunization was conducted every about 2 weeks three times by injecting an emulsion prepared by mixing the immunogen solution and Freund's incomplete adjuvant (DIFCO) in the ratio of 1:1 subcutaneously so that each mouse received about 100 µg of the recombinant hBSSP6 protein each time. Three days after the second booster immunization, blood was collected from the tail vein and the serum antibody titer was measured by ELISA. Two weeks after the third booster immunization, the recombinant hBSSP6 dissolved in physiological saline was administered intraperitoneally so that each mouse received about 100 µg of the recombinant hBSSP6. After 3 days, the spleen cells of immunized mice were used for cell fusion.

(2) ELISA (Direct Solid Phase Method)

A protein solution of the recombinant hBSSP6 protein prepared by the same manner as the preparation of the immunogen was adjusted to 5 µg/ml with PBS and adsorbed on a ELISA plate in an amount of 50 µl/well for 2 hours. After washing 5 times with purified water, the plate was blocked by addition of 4-fold dilution of Blockace™ (Snow Brand Milk Products Co, Ltd.) diluted with PBS. After washing, to the plate was added 50 µl/well of 5000-fold dilution of the serum obtained in the above (1) diluted with serum dilution buffer (PBS containing 5% FBS), followed by reaction at room temperature for 2 hours. After washing, to the plate was added 50 µl/well of 2000-fold dilution of mouse IgG antibody labeled with alkaline phosphatase (INC/Cappel), followed by reaction at room temperature for 2 hours. Separately, a substrate solution was prepared by dissolving disodium p-nitrophenylphosphate (Nitrophenyl Phospate, Disodium, SIGMA 104 phosphatase substrate tablets) in a substrate reaction mixture (9.6% diethanolamine buffer (pH 9.7) containing 0.5 mM magnesium chloride) at concentration of 2 mg/ml. After washing the plate 7 times with purified water, 50 µl/well of the substrate solution was added thereto. After reaction with the substrate solution for 30 minutes, the reaction was ceased by addition of 50 µl of 3N NaOH and the absorbance at 405 nm was measured.

(3) Cell Fusion and Preparation of Hybridoma

Three days after the last immunization, the spleens were excised from three mice whose increase in antibody titer against the recombinant hBSSP6 protein was recognized based on the results of ELISA of the above (2) and spleen cells were prepared according to a conventional manner.

As the parent strain for cell fusion, myeloma SP2 cell strain derived from Balb/c mouse which has been confirmed to be hypoxanthine-guanine-phosphoribosyltransferase (HGPRT) deficient strain beforehand by selecting in a medium containing 20 µg/ml of 8-azaguanine. The cell fusion was carried out according to a conventional manner by mixing $2 \times 10^7$ cells of SP2 cells and $1 \times 10^8$ cells of the spleen cells and using polyethylene glycol 4000 (PEG 4000, Merck) as a fusion promoting agent. After cell fusion, the resultant cells were suspended in Esclon™ medium (Sanko Pure Chemicals) to which hypoxanthine, aminopterin and thymidine were added (HAT medium) at concentration of $3 \times 10^8$ cells/ml and distributed in wells of a 96 well microplate (Corning) in an amount of 100 µl/well. The fused cells were incubated in a $CO_2$ incubator (37° C., 5% $CO_2$) with exchanging a half on the medium every 3 to 5 days. Only hybridomas which could grow in the HAT medium were subjected to selection culture.

(4) Screening of Hybridoma

Wells whose colony formation was confirmed were subjected to screening by using the same ELISA method as that of the above (2) with plates absorbed two kinds of materials, the recombinant hBSSP6 protein, hBSSP6 and trypsinogen to confirm the presence or absence of an antibody specifically reactive with the recombinant hBSSP6 protein in the culture supernatant. Colonies which were strongly reactive with only the recombinant hBSSP6 protein were selected for cloning.

(5) Cloning of Hybridoma

Hybridomas which produced an antibody capable of binding to the recombinant hBSSP6 protein were subjected to cloning three times by limiting dilution method to obtain two hybridomas, FB6MA11 cell strain and FB6MA53 cell strain, which produced antibodies specifically binding to the recombinant hBSSP6 protein and were capable of stable growing.

(6) Typing of Monoclonal Antibody

The isotype was examined by using 0.5 ml portions of the culture supernatants of the above two hybridomas, FB6MA11 cell strain and FB6MA53 cell strain, and Mouse Antibody Isotype kit (Gibco BRL). Both monoclonal antybodies produced by two hybridomas, FB6MA11 cell strain and FB6MA53 cell strain, were H-chain of IgG1 and L-chain of κ.

(7) Preparation of Monoclonal Antibody and Purification Thereof

Eight-week-old female Balb/c mice were received 0.5 ml/mouse of pristane intraperitoneally. After 10 days, about $10^7$ cells/0.5 ml/mouse portions of two hybridomas, FB6MA11 cell strain and FB6MA53 cell strain, obtained in the above cloning (5) were injected intraperitoneally. Since abdominal hypertrophy was recognized from about 10 days after injection, ascites was collected with a 18 G injection needle. The acsites thus collected was centrifuged at 4° C., at 1,000 r.p.m. for 10 minutes. The supernatant was allowed to stand at 37° C. for 30 minutes, followed by further standing at 4° C. overnight. After centrifuging at 4° C., at 12,000 r.p.m. for 10 minutes, the supernatant thus obtained was applied to an affinity column, Sepharose Protein A (Pharmacia Biotech) to purify each monoclonal antibody. Absorbance of a solution of this antibody at 260, 280 and 320 nm was measured ant the concentration of the antibody was determined by werbulg-christian method.

(8) Western Blotting

A sample solution was prepared by mixing the recombinant hBSSP6 protein (pro-form and mature-form(, trypsinogen or human kallikrein with an equal amount of 2×SDA loading buffer (Daiichi Kagaku). The sample solution was subjected to electrophoresis on 10 to 20% polyacrylamide gel (Daiichi Kagaku) by using a SDS electrophoresis apparatus (Daiichi Kagaku) and Tris-glycine buffer (Daiichi Kagaku).

Figure 10:
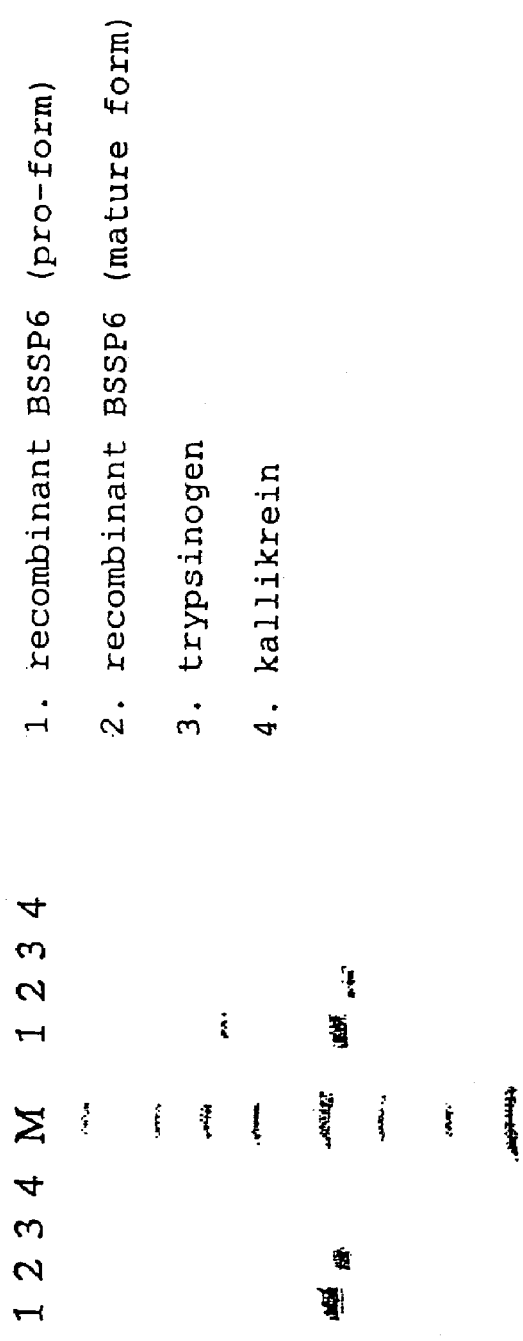
FIG. 10 illustrates the detection of recombinant BSSP6 using the anti-hBSSP6 antibody.
Figure 11:
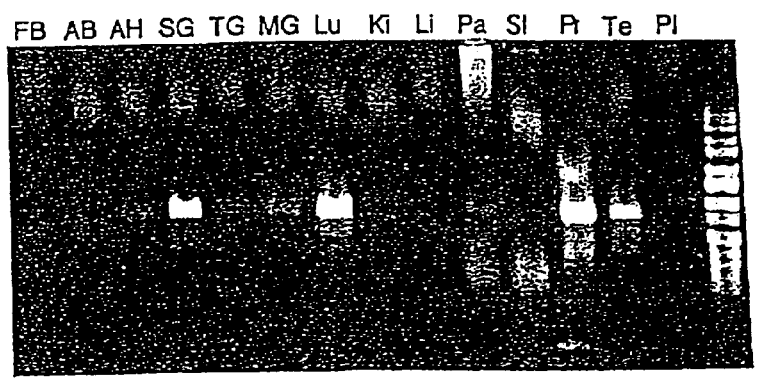
FIG. 11 illustrates the results of RT-PCR of hBSSP6.

On the other hand, 3MM filter paper (Whatman) were dipped in buffer A (Daiichi Kagaku) (2 sheets), in buffer B (Daiichi Kagaku) (1 sheet) and in buffer C (Daiichi Kagaku) (3 sheets), respectively, during electrophoresis. In addition, polyvinylidene difluoride membrane (PVDF membrane: Millipore) was dipped in methanol and then in purified water to adjust itself to water. After electrophoresis, the gel was taken out from the apparatus and the protein was transcribed to the PVDF membrane at 8 mV/cm$^2$ for 1.5 hours by placing two sheets of the filter paper dipped in buffer A, one sheet of the filter paper dipped in buffer B, the PVDF membrane, the gel and three sheets of the filter paper dipped in buffer C in this order from the anode side in a blotter (Pharmacia). After transcription, the PVDF membrane was blocked by shaking with Blockace (Snow Brand Milk Products Co., Ltd.) at room temperature for 1 hour. Then, the membrane was reacted with the purified two antibodies prepared in the above (7) which was diluted with 5% fetal bovine serum-added PBS at 4° C. overnight. Then, an alkaline phosphatase labeled mouse IgG antibody was added and they were reacted at room temperature for 1 hour. Then, the membrane was colored with NBT-BCIP solution to confirm the expression of the recombinant hBSSP6 protein in the culture supernatant (FIG. 10).

EXAMPLE 6

Cloning of Mutant hBSSP6

According to a conventional manner, poly A+RNA was prepared from human prostate cancer cell strain PC-3. This was reverse-transcribed by using Superscript II (Gibco BRL) and oligo dT as the primer to synthesize cDNA. PCR was carried out by using this cDNA as the template and SEQ ID NOS: 20 and 34 as the primers. The reaction was carried out by heating at 95° C. for 2 minutes and repeating a cycle of heating at 95° C. for 30 seconds, at 56° C. for 30 seconds and 72° C. for 30 seconds, 35 times. The resultant PCR product was cloned by using TOPO TA cloning kit and sequenced. As a result, the sequence of mutant hBSSP6 was found. The nucleotide sequence encoding mutant hBSSP6 is shown in SEQ ID NO: 5 and the amino acid sequence of mutant hBSSP6 protein deduced from the nucleotide sequence is shown in SEQ ID NO: 6. In SEQ ID NO: 5, there were two kinds of sequences regarding the 528th to 530th bases encoding the 139th amino acid, Cys, one having the sequence of "tgt" and the other having the sequence of "tgc". Therefore, the 530th base of SEQ ID NO: 5 is represented by "y" which is "t or c". cDNA containing the full length of the mutant type was cloned by using SEQ ID NOS: 20 and 25 to obtain the plasmid pCRII/nBSSP6 variant type.

TABLE 2

| SEQ ID. NO. | Name of primer | Direction | Sequence | Use |
|---|---|---|---|---|
| 20 | hBSSP6F3 | Forward | GGACTCAAGAGAGGAACCTG | FL* |
| 34 | hBSSP6R3 | Reverse | ATGGTGTCTGTGATGTTGCC | for part |
| 25 | hBSSP6R3/P | Reverse | AACTGCAGGAACCAAACACCAAGTGG | FL* |

*for full length

EXAMPLE 7

Expression Analysis of hBSSP6 mRNA by RT-PCR

A transcription reaction was carried out by using poly A+RNA of human various tissues purchased from Clontech as the template and oligo dT primer to obtain cDNA. The reverse transcription reaction was carried out at 55° C. according to the manual of Gibco BRL. PCR was carried out by using this cDNA as the template and primers amplifying an active form and repeating a cycle of heating at 95° C. for 30 seconds, at 60° C. for 30 seconds and at 72° C. for 30 seconds, 35 times. When the PCR product was analyzed by 1% agarose gel electrophoresis, the expression was observed in adult hippocampus, salivary gland, thyroid gland, mammary gland, lung, prostate and testicle.

EXAMPLE 8

Expression of Mutant hBSSP6 by E. coli

A cDNA region encoding the mature type mutant hBSSP6 protein was amplified by PCR using the plasmid pCRII/hBSSP6 variant type as the template and SEQ ID NOS: 21 and 25 as the primers. According to a conventional manner, the PCR product was ligated into pTrc-His B (Invitrogen)

which had been digested with BamHI and blunted with mung bean nuclease. The resultant product was used for transformation of E. coli DH5α and colonies formed were analyzed by PCR to obtain the desired E. coli strain containing the serine protease expressing plasmid pTrcHis/hBSSP6 variant type. The resultant E. coli was designated E. coli pTrcHis/hBSSP6 variant type.

Figure 12:
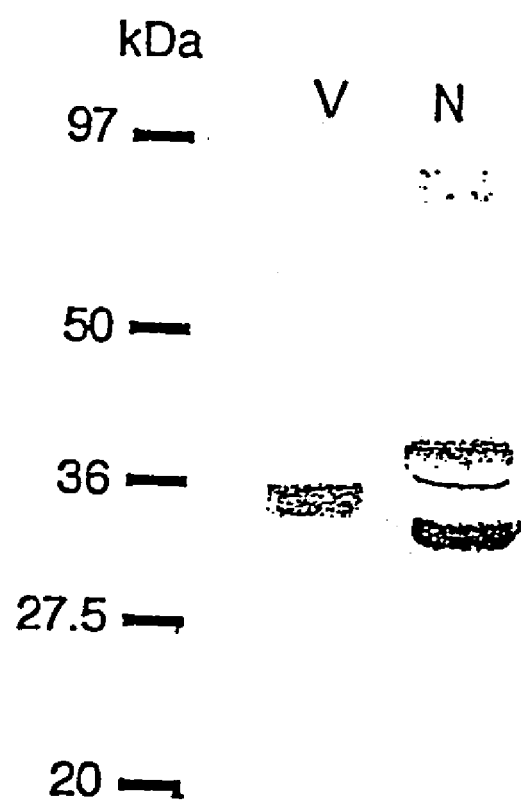
FIG. 12 illustrates the expression of the mutant hBSSP6 in E. coli.

A single colony of E. coli containing the expression plasmid was inoculated in 10 ml of LB (Amp$^+$) medium and incubated at 37° C. overnight. This was inoculated in 250 ml of LB (Amp$^+$) and incubated at 37° C. When the absorbance at 600 nm became 0.5, 250 μl of 0.1 M IPTG (isopropyl-β-D(-)thiogalactopyranoside) was added and incubation was continued additional 5 hours. After centrifuging the E. coli, it was-suspended in a cell disruption buffer (10 mM phosphate buffer pH 7.5, 1 mM EDTA) and the suspension was sonicated on ice to disrupt E. coli. The resultant was centrifuged at 4° C., at 14,000 r.p.m. for 20 minutes to obtain a precipitate. The precipitate was washed twice with the cell disruption buffer containing 0.5% Triton X-100. After washing with water to removed Triton X-10, the precipitate was soaked in a denaturation buffer containing 8 M urea (8 M urea, 50 mM Tris, pH 8.5, 20 mM 2ME) at 37° C. for 1 hour to dissolve it. The solution was passed through TALON metal affinity resin (Clontech) and, after washing with the denaturation buffer containing 10 mM imidazole, the resin was elated with the denaturation buffer containing 100 mM imidazole to purify it. When the purified material was detected by anti-hBSSP6 antibody, a band specific for the mutant type having a higher molecular weight than hBSSP6 was detected (FIG. 12). According to the procedure of Example 4, mutant hBSSP6 can be expressed by using Sf-9 cells to examine its enzyme activity.

TABLE 3

| SEQ ID NO: | Name of primer | Direction | Sequence | Use |
|---|---|---|---|---|
| 21 | hBSSP6F4 | Forward | ATCATCAAGGGGTTCGAGTG | for part |

EXAMPLE 9

Detection of Mutant hBSSP6 mRNA by RT-PCR and Southern Hybridization

Figure 13:
FIG. 13 illustrates the results of PCR-southern hybridization of a mutant specific RT-PCR product using a hBSSP6 probe.

A transcription reaction was carried out by using poly A+RNA of human various tissues purchased from Clontech as the template and oligo dT primer to obtain cDNA. The reverse transcription reaction was carried out at 55° C. according to the manual of Gibco BRL. PCR was carried out by using this cDNA as the template and SEQ ID NOS: 20 and 35 as the primers and repeating a cycle of heating at 95° C. for 30 seconds, at 60° C. for 30 seconds and at 72° C. for 30 seconds, 30 times. The PCR product thus obtained was blotted on nylon membrane (Hybond N+, Amersham-Pharmacia). At this time, pCRII/hBSSP6 variant type cleaved by the restriction enzyme EcoRI was blotted as a control. A probe was prepared separately by labeling a part of a nucleotide sequence encoding the full length of pCR II/hBSSP6 with α-$^{32}$P dCTP. The probe was diluted with 5×SSC and reacted with the above membrane filter at 65° C. for a whole day and night. Then, the membrane filter was washed twice each with 2×SSC/0.1% SDS at room temperature for 30 minutes, 1×SSC/0.1% SDS at room temperature for 30 minutes and 0.1×SSC/0.1% SDS at 65° C. for 30 minutes. The filter was exposed to an imaging plate for FLA2000 (Fuji Film) for one day. As a result, expression was observed in prostate cancer cell strains, PC-3, DU145, and LNCaP examined, as well as in testicle, lung, fetus brain, and adult hippocampus of human beings (FIG. 13).

TABLE 4

| SEQ ID NO: | Name of primer | Direction | Sequence | Use |
|---|---|---|---|---|
| 35 | hBSSP6F7 | Forward | CCTCAAGCCGTGGGTGTCAC | for part |

INDUSTRIAL UTILITY

According to the present invention, there are provided isolated human and mouse serine protease (hBSSP6 and mBSSP6) polynucleotides, their homologous forms, mature forms, precursors and polymorphic variants. Further, according to the present invention, there are provided hBSSP6 and mBSSP6 proteins as well as compositions containing hBSSP6 and mBSSP6 polynucleotides and proteins, their production and use.

Sequence Listing Free Text

SEQ ID NO: 7: Designed oligonucleotide to construct plasmid pSecTrypHis

SEQ ID NO: 8: Designed oligonucleotide to construct plasmid pSecTrypHis

SEQ ID NO: 9: Designed oligonucleotide primer to amplify neurosin-encoding sequence SEQ ID NO:10: Designed oligonucleotide primer to amplify neurosin-encoding sequence SEQ ID NO:11: Designed oligonucleotide primer to amplify a portion of plasmid pSecTrypHis/Neurosin SEQ ID NO:12: Designed oligonucleotide primer to amplify a portion of plasmid pSecTrypHis/Neurosin SEQ ID NO:13: Designed oligonucleotide primer to amplify a portion of plasmid pTrypHis SEQ ID NO:14: Designed oligonucleotide primer to amplify a portion of plasmid pTrypSigTag SEQ ID NO:15: Designed oligonucleotide primer to amplify a portion of plasmid pFBTrypSigTag SEQ ID NO:16: Designed oligonucleotide primer to amplify active hBSSP6-encoding sequence SEQ ID NO:17: Designed oligonucleotide primer to amplify active hBSSP6-encoding sequence SEQ ID NO:18: Designed oligonucleotide primer designated as hBSSP6F1 for RACE for human BSSP6 (forward)

SEQ ID NO:19: Designed oligonucleotide primer designated as hBSSP6F2 for RACE for human BSSP6 (forward)

SEQ ID NO:20: Designed oligonucleotide primer designated as hBSSP6F3 to amplify full-length human brain BSSP6-encoding mRNA (forward)

SEQ ID NO:21: Designed oligonucleotide primer designated as hBSSP6F4 to amplify mature human BSSP6-encoding region (forward)

SEQ ID NO:22: Designed oligonucleotide primer designated as hBSSP6F5 to amplify full-length human prostate BSSP6-encoding mRNA (forward)

SEQ ID NO:23: Designed oligonucleotide primer designated as hBSSP6R1 for RACE for human BSSP6 (reverse)

SEQ ID NO:24: Designed oligonucleotide primer designated as hBSSP6R2 for RACE for human BSSP6 (reverse)

SEQ ID NO:25: Designed oligonucleotide primer designated as hBSSP6R3/P to amplify full-length human BSSP6-encoding mRNA (reverse)

SEQ ID NO:26: Designed oligonucleotide primer designated as mBSSP6F1 for RACE for mouse BSSP6 (forward)

SEQ ID NO:27: Designed oligonucleotide primer designated as mBSSP6F2 for RACE for mouse BSSP6 (forward)

SEQ ID NO:28: Designed oligonucleotide primer designated as mBSSP6F3 to amplify full-length mouse prostate BSSP6-encoding mRNA (forward)

SEQ ID NO:29: Designed oligonucleotide primer designated as mBSSP6F4 to amplify mature mouse BSSP6-encoding region (forward)

SEQ ID NO:30: Designed oligonucleotide primer designated as mBSSP6F5 to amplify full-length mouse brain BSSP6-encoding mRNA (forward)

SEQ ID NO:31: Designed oligonucleotide primer designated as mBSSP6R1 for RACE for mouse BSSP6 (reverse)

SEQ ID NO:32: Designed oligonucleotide primer designated as mBSSP6R2 for RACE for mouse BSSP6 (reverse)

SEQ ID NO:33: Designed oligonucleotide primer designated as mBSSP6R3/E to amplify full-length mouse BSSP6-encoding mRNA (reverse)

SEQ ID NO:34: Designed oligonucleotide primer designated as hBSSP6R3 to amplify a portion of BSSP6 variant type-encoding mRNA from human prostatic cancer cell line PC-3 (reverse)

SEQ ID NO:35: Designed oligonucleotide primer designated as hBSSP6F7 to amplify a portion of human BSSP6-encoding mRNA (forward)

SEQ ID NO:36: Designed oligonucleotide primer to amplify conserved region of serine proteases-encoding sequence; n is a, c, g or t.

SEQ ID NO:37: Designed oligonucleotide primer to amplify conserved region of serine proteases-encoding sequence; n is a, c, g or t.

What is claimed is:

1. A polynucleotide consisting of the full length nucleotide sequence of SEQ ID NO:1.

2. A vector comprising the polynucleotide according to claim 1.

3. A isolated host cell trasformed whith the polynucleotide according to claim 1 in an expressible state.

* * * * *

SEQUENCE LISTING

```
<160> NUMBER OF SEQ ID NOS: 41

<210> SEQ ID NO 1
<211> LENGTH: 1301
<212> TYPE: DNA
<213> ORGANISM: Homo sapiens
<220> FEATURE:
<221> NAME/KEY: CDS
<222> LOCATION: (113)..(958)
<223> OTHER INFORMATION:
<220> FEATURE:
<221> NAME/KEY: mat_peptide
<222> LOCATION: (272)..()
<223> OTHER INFORMATION:

<400> SEQUENCE: 1
ctgccttgct ccacacctgg tcaggggaga gaggggagga aagccaaggg aagggaccta      60
actgaaaaca aacaagctgg gagaagcagg aatctgcgct cgggttccgc ag atg cag     118
                                                          Met Gln agg ttg agg tgg ctg cgg gac tgg aag tca tcg ggc aga ggt ctc aca       166
Arg Leu Arg Trp Leu Arg Asp Trp Lys Ser Ser Gly Arg Gly Leu Thr
    -50                 -45                 -40 gca gcc aag gaa cct ggg gcc cgc tcc tcc ccc ctc cag gcc atg agg       214
Ala Ala Lys Glu Pro Gly Ala Arg Ser Ser Pro Leu Gln Ala Met Arg
-35                 -30                 -25                 -20 att ctg cag tta atc ctg ctt gct ctg gca aca ggg ctt gta ggg gga       262
Ile Leu Gln Leu Ile Leu Leu Ala Leu Ala Thr Gly Leu Val Gly Gly
                -15                 -10                  -5 gag acc agg atc atc aag ggg ttc gag tgc aag cct cac tcc cag ccc       310
Glu Thr Arg Ile Ile Lys Gly Phe Glu Cys Lys Pro His Ser Gln Pro
     -1   1                   5                  10 tgg cag gca gcc ctg ttc gag aag acg cgg cta ctc tgt ggg gcg acg       358
Trp Gln Ala Ala Leu Phe Glu Lys Thr Arg Leu Leu Cys Gly Ala Thr
         15                  20                  25 ctc atc gcc ccc aga tgg ctc ctg aca gca gcc cac tgc ctc aag ccc       406
Leu Ile Ala Pro Arg Trp Leu Leu Thr Ala Ala His Cys Leu Lys Pro
 30                  35                  40                  45 cgc tac ata gtt cac ctg ggg cag cac aac ctc cag aag gag gag ggc       454
Arg Tyr Ile Val His Leu Gly Gln His Asn Leu Gln Lys Glu Glu Gly
                 50                  55                  60 tgt gag cag acc cgg aca gcc act gag tcc ttc ccc cac ccc ggc ttc       502
Cys Glu Gln Thr Arg Thr Ala Thr Glu Ser Phe Pro His Pro Gly Phe
```

-continued

| | | | | | | | | | | | | | | |
|---|---|---|---|---|---|---|---|---|---|---|---|---|---|---|
| | | | 65 | | | | 70 | | | | 75 | | | |
| aac | aac | agc | ctc | ccc | aac | aaa | gac | cac | cgc | aat | gac | atc | atg ctg gtg | 550 |
| Asn | Asn | Ser | Leu | Pro | Asn | Lys | Asp | His | Arg | Asn | Asp | Ile | Met Leu Val | |
| | | 80 | | | | 85 | | | | 90 | | | | |
| aag | atg | gca | tcg | cca | gtc | tcc | atc | acc | tgg | gct | gtg | cga | ccc ctc acc | 598 |
| Lys | Met | Ala | Ser | Pro | Val | Ser | Ile | Thr | Trp | Ala | Val | Arg | Pro Leu Thr | |
| 95 | | | | 100 | | | | 105 | | | | | | |
| ctc | tcc | tca | cgc | tgt | gtc | act | gct | ggc | acc | agc | tgc | ctc | att tcc ggc | 646 |
| Leu | Ser | Ser | Arg | Cys | Val | Thr | Ala | Gly | Thr | Ser | Cys | Leu | Ile Ser Gly | |
| 110 | | | | 115 | | | | 120 | | | | 125 | | |
| tgg | ggc | agc | acg | tcc | agc | ccc | cag | tta | cgc | ctg | cct | cac | acc ttg cga | 694 |
| Trp | Gly | Ser | Thr | Ser | Ser | Pro | Gln | Leu | Arg | Leu | Pro | His | Thr Leu Arg | |
| | | | 130 | | | | 135 | | | | 140 | | | |
| tgc | gcc | aac | atc | acc | atc | att | gag | cac | cag | aag | tgt | gag | aac gcc tac | 742 |
| Cys | Ala | Asn | Ile | Thr | Ile | Ile | Glu | His | Gln | Lys | Cys | Glu | Asn Ala Tyr | |
| | | | 145 | | | | 150 | | | | 155 | | | |
| ccc | ggc | aac | atc | aca | gac | acc | atg | gtg | tgt | gcc | agc | gtg | cag gaa ggg | 790 |
| Pro | Gly | Asn | Ile | Thr | Asp | Thr | Met | Val | Cys | Ala | Ser | Val | Gln Glu Gly | |
| | | | 160 | | | | 165 | | | | 170 | | | |
| ggc | aag | gac | tcc | tgc | cag | ggt | gac | tcc | ggg | ggc | cct | ctg | gtc tgt aac | 838 |
| Gly | Lys | Asp | Ser | Cys | Gln | Gly | Asp | Ser | Gly | Gly | Pro | Leu | Val Cys Asn | |
| | 175 | | | | 180 | | | | 185 | | | | | |
| cag | tct | ctt | caa | ggc | att | atc | tcc | tgg | ggc | cag | gat | ccg | tgt gcg atc | 886 |
| Gln | Ser | Leu | Gln | Gly | Ile | Ile | Ser | Trp | Gly | Gln | Asp | Pro | Cys Ala Ile | |
| 190 | | | | 195 | | | | 200 | | | | | | 205 |
| acc | cga | aag | cct | ggt | gtc | tac | acg | aaa | gtc | tgc | aaa | tat | gtg gac tgg | 934 |
| Thr | Arg | Lys | Pro | Gly | Val | Tyr | Thr | Lys | Val | Cys | Lys | Tyr | Val Asp Trp | |
| | | | 210 | | | | 215 | | | | 220 | | | |
| atc | cag | gag | acg | atg | aag | aac | aat | tagactggac | | ccacccacca | | cagcccatca | | | 988 |
| Ile | Gln | Glu | Thr | Met | Lys | Asn | Asn | | | | | | | |
| | | | 225 | | | | | | | | | | | |

```
ccctccattt  ccacttggtg  tttggttcct  gttcactctg  ttaataagaa  accctaagcc    1048
aagaccctct  acgaacattc  tttgggcctc  ctggactaca  ggagatgctg  tcacttaata    1108
atcaacctgg  ggttcgaaat  cagtgagacc  tggattcaaa  ttctgccttg  aaatattgtg    1168
actctgggaa  tgacaacacc  tggtttgttc  tctgttgtat  ccccagcccc  aaagacagct    1228
cctggccata  tatcaaggtt  tcaataaata  tttgctaaat  gaaaaaaaaa  aaaaaaaaa     1288 aaaaaaaaaa  aaa                                                          1301

<210> SEQ ID NO 2
<211> LENGTH: 282
<212> TYPE: PRT
<213> ORGANISM: Homo sapiens

<400> SEQUENCE: 2
```

| | | | | | | | | | | | | | |
|---|---|---|---|---|---|---|---|---|---|---|---|---|---|
| Met | Gln | Arg | Leu | Arg | Trp | Leu | Arg | Asp | Trp | Lys | Ser | Ser | Gly Arg Gly |
| | | | -50 | | | | -45 | | | | -40 | | |
| Leu | Thr | Ala | Ala | Lys | Glu | Pro | Gly | Ala | Arg | Ser | Ser | Pro | Leu Gln Ala |
| | | -35 | | | | -30 | | | | -25 | | | |
| Met | Arg | Ile | Leu | Gln | Leu | Ile | Leu | Leu | Ala | Leu | Ala | Thr | Gly Leu Val |
| | -20 | | | | -15 | | | | -10 | | | | |
| Gly | Gly | Glu | Thr | Arg | Ile | Ile | Lys | Gly | Phe | Glu | Cys | Lys | Pro His Ser |
| -5 | | | | -1 | 1 | | | 5 | | | | 10 | |
| Gln | Pro | Trp | Gln | Ala | Ala | Leu | Phe | Glu | Lys | Thr | Arg | Leu | Leu Cys Gly |
| | | | 15 | | | | 20 | | | | 25 | | |
| Ala | Thr | Leu | Ile | Ala | Pro | Arg | Trp | Leu | Leu | Thr | Ala | Ala | His Cys Leu |
| | | 30 | | | | 35 | | | | 40 | | | |

```
Lys Pro Arg Tyr Ile Val His Leu Gly Gln His Asn Leu Gln Lys Glu
     45                  50                  55
Glu Gly Cys Glu Gln Thr Arg Thr Ala Thr Glu Ser Phe Pro His Pro
 60                  65                  70                  75
Gly Phe Asn Asn Ser Leu Pro Asn Lys Asp His Arg Asn Asp Ile Met
                 80                  85                  90
Leu Val Lys Met Ala Ser Pro Val Ser Ile Thr Trp Ala Val Arg Pro
                 95                 100                 105
Leu Thr Leu Ser Ser Arg Cys Val Thr Ala Gly Thr Ser Cys Leu Ile
            110                 115                 120
Ser Gly Trp Gly Ser Thr Ser Ser Pro Gln Leu Arg Leu Pro His Thr
            125                 130                 135
Leu Arg Cys Ala Asn Ile Thr Ile Ile Glu His Gln Lys Cys Glu Asn
140                 145                 150                 155
Ala Tyr Pro Gly Asn Ile Thr Asp Thr Met Val Cys Ala Ser Val Gln
                160                 165                 170
Glu Gly Gly Lys Asp Ser Cys Gln Gly Asp Ser Gly Gly Pro Leu Val
            175                 180                 185
Cys Asn Gln Ser Leu Gln Gly Ile Ile Ser Trp Gly Gln Asp Pro Cys
            190                 195                 200
Ala Ile Thr Arg Lys Pro Gly Val Tyr Thr Lys Val Cys Lys Tyr Val
            205                 210                 215
Asp Trp Ile Gln Glu Thr Met Lys Asn Asn
220                 225

<210> SEQ ID NO 3
<211> LENGTH: 1323
<212> TYPE: DNA
<213> ORGANISM: Mus sp.
<220> FEATURE:
<221> NAME/KEY: CDS
<222> LOCATION: (103)..(930)
<223> OTHER INFORMATION:
<220> FEATURE:
<221> NAME/KEY: mat_peptide
<222> LOCATION: (244)..()
<223> OTHER INFORMATION:

<400> SEQUENCE: 3
ccacatctga ctagggaagt aaggcgaagg aggcccatgg aagaaaaatc taaatgaaaa      60
cataagctag gagaactgag gcttcaaacc tgaagctatc ta atg agg agg ctg       114
                                                 Met Arg Arg Leu
                                                             -45 aag agt gac tgg aaa tta tct aca gaa acc agg gaa cct ggc gcc cgc      162
Lys Ser Asp Trp Lys Leu Ser Thr Glu Thr Arg Glu Pro Gly Ala Arg
        -40                 -35                 -30 cct gcc cta ctc cag gcc agg atg att ctc cga ctc att gca ctt gct      210
Pro Ala Leu Leu Gln Ala Arg Met Ile Leu Arg Leu Ile Ala Leu Ala
        -25                 -20                 -15 ctg gta aca ggg cac gta ggg gga gag acg agg atc atc aag ggt tat      258
Leu Val Thr Gly His Val Gly Gly Glu Thr Arg Ile Ile Lys Gly Tyr
-10                  -5                  -1   1                5 gag tgc agg cct cac tca cag cca tgg cag gtg gcc ctc ttt cag aag      306
Glu Cys Arg Pro His Ser Gln Pro Trp Gln Val Ala Leu Phe Gln Lys
                10                  15                  20 aca cgg ctt ctc tgt ggg gca acc ctc atc gcc ccc aaa tgg ctc ctg      354
Thr Arg Leu Leu Cys Gly Ala Thr Leu Ile Ala Pro Lys Trp Leu Leu
            25                  30                  35
```

```
aca gca gcc cac tgc cgc aag ccc cat tac gtg atc ctc ctt gga gag    402
Thr Ala Ala His Cys Arg Lys Pro His Tyr Val Ile Leu Leu Gly Glu
         40                  45                  50 cac aat cta gag aag aca gac ggc tgt gag cag agg cgg atg gcc act    450
His Asn Leu Glu Lys Thr Asp Gly Cys Glu Gln Arg Arg Met Ala Thr
 55                  60                  65 gag tcc ttc ccc cac ccc gac ttc aac aac agc ctc ccc aac aaa gac    498
Glu Ser Phe Pro His Pro Asp Phe Asn Asn Ser Leu Pro Asn Lys Asp
 70                  75                  80                  85 cac cgg aat gac ata atg ctt gtg aag atg tcg tct ccc gtc ttc ttt    546
His Arg Asn Asp Ile Met Leu Val Lys Met Ser Ser Pro Val Phe Phe
                 90                  95                 100 acc cga gct gtg cag cca ctc acc ctg tcc cca cac tgt gtc gct gca    594
Thr Arg Ala Val Gln Pro Leu Thr Leu Ser Pro His Cys Val Ala Ala
                105                 110                 115 ggc acc agc tgc ctc att tct gga tgg ggc acc acg tcc agc ccc cag    642
Gly Thr Ser Cys Leu Ile Ser Gly Trp Gly Thr Thr Ser Ser Pro Gln
        120                 125                 130 ttg cgc ctg cct cat tcc ttg cga tgt gcc aat gtc tcc atc atc gaa    690
Leu Arg Leu Pro His Ser Leu Arg Cys Ala Asn Val Ser Ile Ile Glu
135                 140                 145 cac aag gag tgt gag aag gcc tac ccg ggc aac atc aca gac acc atg    738
His Lys Glu Cys Glu Lys Ala Tyr Pro Gly Asn Ile Thr Asp Thr Met
150                 155                 160                 165 ctg tgc gcc agt gtt cgg aaa gag ggc aag gac tcc tgt cag ggt gac    786
Leu Cys Ala Ser Val Arg Lys Glu Gly Lys Asp Ser Cys Gln Gly Asp
                170                 175                 180 tct gga ggc ccc ctg gtc tgc aac gga tct ctt caa ggc atc atc tcc    834
Ser Gly Gly Pro Leu Val Cys Asn Gly Ser Leu Gln Gly Ile Ile Ser
            185                 190                 195 tgg ggt cag gac cca tgt gcc gtc acc aga aag cct ggt gtc tat aca    882
Trp Gly Gln Asp Pro Cys Ala Val Thr Arg Lys Pro Gly Val Tyr Thr
        200                 205                 210 aaa gtc tgc aaa tac ttt aac tgg atc cac gag gtt atg agg aac aat    930
Lys Val Cys Lys Tyr Phe Asn Trp Ile His Glu Val Met Arg Asn Asn
215                 220                 225 tagaggggac ctgcttccca ccacccaacc cctccaacct cttcttaatg ctttgacttc    990
tcttcattct gccctaagaa gtcctcagct gggaccctgg catgtactct ctccgaccca   1050
ccatgagtat agtataggga tgctctaact tgatgatcga cctggggcct ggaatcaaat   1110
cctgacttga actaaattgt gactctggac atgatcacca ctggttttgt ttgtttggtt   1170
gttttttgtt ttgttttgtt ttgttcccag ctttgaagac agtccctggc atatcccagg   1230
gtttcaataa atatttgtta aatgataaaa aaaaaaaaa  aaaaaaaaa  aaaaaaaaa    1290 aaaaaaaaaa aaaaaaaaaa aaaaaaaaaa aaa                                1323

<210> SEQ ID NO 4
<211> LENGTH: 276
<212> TYPE: PRT
<213> ORGANISM: Mus sp.

<400> SEQUENCE: 4

Met Arg Arg Leu Lys Ser Asp Trp Lys Leu Ser Thr Glu Thr Arg Glu
         -45                 -40                 -35

Pro Gly Ala Arg Pro Ala Leu Gln Ala Arg Met Ile Leu Arg Leu
     -30                 -25                 -20

Ile Ala Leu Ala Leu Val Thr Gly His Val Gly Gly Glu Thr Arg Ile
-15                 -10                  -5              -1   1
```

```
Ile Lys Gly Tyr Glu Cys Arg Pro His Ser Gln Pro Trp Gln Val Ala
            5                   10                  15
Leu Phe Gln Lys Thr Arg Leu Leu Cys Gly Ala Thr Leu Ile Ala Pro
        20                  25                  30
Lys Trp Leu Leu Thr Ala Ala His Cys Arg Lys Pro His Tyr Val Ile
35                  40                  45
Leu Leu Gly Glu His Asn Leu Glu Lys Thr Asp Gly Cys Glu Gln Arg
50                  55                  60                  65
Arg Met Ala Thr Glu Ser Phe Pro His Pro Asp Phe Asn Asn Ser Leu
                70                  75                  80
Pro Asn Lys Asp His Arg Asn Asp Ile Met Leu Val Lys Met Ser Ser
            85                  90                  95
Pro Val Phe Phe Thr Arg Ala Val Gln Pro Leu Thr Leu Ser Pro His
            100                 105                 110
Cys Val Ala Ala Gly Thr Ser Cys Leu Ile Ser Gly Trp Gly Thr Thr
            115                 120                 125
Ser Ser Pro Gln Leu Arg Leu Pro His Ser Leu Arg Cys Ala Asn Val
130                 135                 140                 145
Ser Ile Ile Glu His Lys Glu Cys Glu Lys Ala Tyr Pro Gly Asn Ile
                150                 155                 160
Thr Asp Thr Met Leu Cys Ala Ser Val Arg Lys Glu Gly Lys Asp Ser
                165                 170                 175
Cys Gln Gly Asp Ser Gly Gly Pro Leu Val Cys Asn Gly Ser Leu Gln
            180                 185                 190
Gly Ile Ile Ser Trp Gly Gln Asp Pro Cys Ala Val Thr Arg Lys Pro
            195                 200                 205
Gly Val Tyr Thr Lys Val Cys Lys Tyr Phe Asn Trp Ile His Glu Val
210                 215                 220                 225
Met Arg Asn Asn

<210> SEQ ID NO 5
<211> LENGTH: 934
<212> TYPE: DNA
<213> ORGANISM: Homo sapiens
<220> FEATURE:
<221> NAME/KEY: CDS
<222> LOCATION: (51)..(875)
<223> OTHER INFORMATION:
<220> FEATURE:
<221> NAME/KEY: mat_peptide
<222> LOCATION: (114)..()
<223> OTHER INFORMATION:

<400> SEQUENCE: 5
actgggactc aagagaggaa cctggggccc gctcctcccc cctccaggcc atg agg        56
                                                         Met Arg
                                                         -20 att ctg cag tta atc ctg ctt gct ctg gca aca ggg ctt gta ggg gga     104
Ile Leu Gln Leu Ile Leu Leu Ala Leu Ala Thr Gly Leu Val Gly Gly
            -15                 -10                 -5 gag acc agg atc atc aag ggg ttc gag tgc aag cct cac tcc cag ccc     152
Glu Thr Arg Ile Ile Lys Gly Phe Glu Cys Lys Pro His Ser Gln Pro
    -1   1                   5                   10 tgg cag gca gcc ctg ttc gag aag acg cgg cta ctc tgt ggg gcg acg     200
Trp Gln Ala Ala Leu Phe Glu Lys Thr Arg Leu Leu Cys Gly Ala Thr
            15                  20                  25 ctc atc gcc ccc aga tgg ctc ctg aca gca gcc cac tgc ctc aag ccg     248
Leu Ile Ala Pro Arg Trp Leu Leu Thr Ala Ala His Cys Leu Lys Pro
30                  35                  40                  45
```

-continued

```
tgg gtg tca ctc acc tct ccc acc cat gtc tcc ccc gac ctt tcc tcc      296
Trp Val Ser Leu Thr Ser Pro Thr His Val Ser Pro Asp Leu Ser Ser
             50                  55                  60 tcc aac tac tgt ctc tcc cac ctc agc cgc tac ata gtt cac ctg ggg      344
Ser Asn Tyr Cys Leu Ser His Leu Ser Arg Tyr Ile Val His Leu Gly
         65                  70                  75 cag cac aac ctc cag aag gag gag ggc tgt gag cag acc cgg aca gcc      392
Gln His Asn Leu Gln Lys Glu Glu Gly Cys Glu Gln Thr Arg Thr Ala
     80                  85                  90 act gag tcc ttc ccc cac ccc ggc ttc aac aac agc ctc ccc aac aaa      440
Thr Glu Ser Phe Pro His Pro Gly Phe Asn Asn Ser Leu Pro Asn Lys
 95                 100                 105 gac cac cgc aat gac atc atg ctg gtg aag atg gca tcg cca gtc tcc      488
Asp His Arg Asn Asp Ile Met Leu Val Lys Met Ala Ser Pro Val Ser
110                 115                 120                 125 atc acc tgg gct gtg cga ccc ctc acc ctc tcc tca cgc tgy gtc act      536
Ile Thr Trp Ala Val Arg Pro Leu Thr Leu Ser Ser Arg Cys Val Thr
             130                 135                 140 gct ggc acc agc tgc ctc att tcc ggc tgg ggc agc acg tcc agc ccc      584
Ala Gly Thr Ser Cys Leu Ile Ser Gly Trp Gly Ser Thr Ser Ser Pro
         145                 150                 155 cag tta cgc ctg cct cac acc ttg cga tgc gcc aac atc acc atc att      632
Gln Leu Arg Leu Pro His Thr Leu Arg Cys Ala Asn Ile Thr Ile Ile
     160                 165                 170 gag cac cag aag tgt gag aac gcc tac ccc ggc aac atc aca gac acc      680
Glu His Gln Lys Cys Glu Asn Ala Tyr Pro Gly Asn Ile Thr Asp Thr
175                 180                 185 atg gtg tgt gcc agc gtg cag gaa ggg ggc aag gac tcc tgc cag ggt      728
Met Val Cys Ala Ser Val Gln Glu Gly Gly Lys Asp Ser Cys Gln Gly
190                 195                 200                 205 gac tcc ggg ggc cct ctg gtc tgt aac cag tct ctt caa ggc att atc      776
Asp Ser Gly Gly Pro Leu Val Cys Asn Gln Ser Leu Gln Gly Ile Ile
             210                 215                 220 tcc tgg ggc cag gat ccg tgt gcg atc acc cga aag cct ggt gtc tac      824
Ser Trp Gly Gln Asp Pro Cys Ala Ile Thr Arg Lys Pro Gly Val Tyr
         225                 230                 235 acg aaa gtc tgc aaa tat gtg gac tgg atc cag gag acg atg aag aac      872
Thr Lys Val Cys Lys Tyr Val Asp Trp Ile Gln Glu Thr Met Lys Asn
     240                 245                 250 aat tagactggac ccacccacca cagcccatca ccctccattt ccacttggtg           925
Asn tttggttcc                                                            934
```

<210> SEQ ID NO 6
<211> LENGTH: 275
<212> TYPE: PRT
<213> ORGANISM: Homo sapiens

<400> SEQUENCE: 6

```
Met Arg Ile Leu Gln Leu Ile Leu Leu Ala Leu Ala Thr Gly Leu Val
        -20                 -15                 -10

Gly Gly Glu Thr Arg Ile Ile Lys Gly Phe Glu Cys Lys Pro His Ser
 -5                  -1  1                   5                  10

Gln Pro Trp Gln Ala Ala Leu Phe Glu Lys Thr Arg Leu Leu Cys Gly
             15                  20                  25

Ala Thr Leu Ile Ala Pro Arg Trp Leu Leu Thr Ala Ala His Cys Leu
         30                  35                  40

Lys Pro Trp Val Ser Leu Thr Ser Pro Thr His Val Ser Pro Asp Leu
```

```
            45                  50                  55
Ser Ser Ser Asn Tyr Cys Leu Ser His Leu Ser Arg Tyr Ile Val His
 60                  65                  70                  75

Leu Gly Gln His Asn Leu Gln Lys Glu Glu Gly Cys Glu Gln Thr Arg
                 80                  85                  90

Thr Ala Thr Glu Ser Phe Pro His Pro Gly Phe Asn Asn Ser Leu Pro
             95                 100                 105

Asn Lys Asp His Arg Asn Asp Ile Met Leu Val Lys Met Ala Ser Pro
        110                 115                 120

Val Ser Ile Thr Trp Ala Val Arg Pro Leu Thr Leu Ser Ser Arg Cys
125                 130                 135

Val Thr Ala Gly Thr Ser Cys Leu Ile Ser Gly Trp Gly Ser Thr Ser
140                 145                 150                 155

Ser Pro Gln Leu Arg Leu Pro His Thr Leu Arg Cys Ala Asn Ile Thr
                160                 165                 170

Ile Ile Glu His Gln Lys Cys Glu Asn Ala Tyr Pro Gly Asn Ile Thr
            175                 180                 185

Asp Thr Met Val Cys Ala Ser Val Gln Glu Gly Gly Lys Asp Ser Cys
        190                 195                 200

Gln Gly Asp Ser Gly Gly Pro Leu Val Cys Asn Gln Ser Leu Gln Gly
    205                 210                 215

Ile Ile Ser Trp Gly Gln Asp Pro Cys Ala Ile Thr Arg Lys Pro Gly
220                 225                 230                 235

Val Tyr Thr Lys Val Cys Lys Tyr Val Asp Trp Ile Gln Glu Thr Met
                240                 245                 250

Lys Asn Asn

<210> SEQ ID NO 7
<211> LENGTH: 99
<212> TYPE: DNA
<213> ORGANISM: Artificial Sequence
<220> FEATURE:
<223> OTHER INFORMATION: Designed oligonucleotide to construct plasmid
      pSecTrypHis

<400> SEQUENCE: 7
aagcttggct agcaacacca tgaatctact cctgatcctt acctttgttg ctgctgctgt    60
tgctgccccc tttgacgacg atgacaagga tccgaattc                          99

<210> SEQ ID NO 8
<211> LENGTH: 99
<212> TYPE: DNA
<213> ORGANISM: Artificial Sequence
<220> FEATURE:
<223> OTHER INFORMATION: Designed oligonucleotide to construct plasmid
      pSecTrypHis

<400> SEQUENCE: 8
gaattcggat ccttgtcatc gtcgtcaaag ggggcagcaa cagcagcagc aacaaaggta    60
aggatcagga gtagattcat ggtgttgcta gccaagctt                          99

<210> SEQ ID NO 9
<211> LENGTH: 15
<212> TYPE: DNA
<213> ORGANISM: Artificial Sequence
<220> FEATURE:
<223> OTHER INFORMATION: Designed oligonucleotide primer to amplify
      neurosin-encoding sequence
```

```
<400> SEQUENCE: 9
ttggtgcatg gcgga                                                    15

<210> SEQ ID NO 10
<211> LENGTH: 27
<212> TYPE: DNA
<213> ORGANISM: Artificial Sequence
<220> FEATURE:
<223> OTHER INFORMATION: Designed oligonucleotide primer to amplify
      neurosin-encoding sequence

<400> SEQUENCE: 10
tcctcgagac ttggcctgaa tggtttt                                       27

<210> SEQ ID NO 11
<211> LENGTH: 35
<212> TYPE: DNA
<213> ORGANISM: Artificial Sequence
<220> FEATURE:
<223> OTHER INFORMATION: Designed oligonucleotide primer to amplify
      a portion of plasmid pSecTrypHis/Neurosin

<400> SEQUENCE: 11
gcgctagcag atctccatga atctactcct gatcc                              35

<210> SEQ ID NO 12
<211> LENGTH: 29
<212> TYPE: DNA
<213> ORGANISM: Artificial Sequence
<220> FEATURE:
<223> OTHER INFORMATION: Designed oligonucleotide primer to amplify
      a portion of plasmid pSecTrypHis/Neurosin

<400> SEQUENCE: 12
tgaagcttgc catggaccaa cttgtcatc                                     29

<210> SEQ ID NO 13
<211> LENGTH: 26
<212> TYPE: DNA
<213> ORGANISM: Artificial Sequence
<220> FEATURE:
<223> OTHER INFORMATION: Designed oligonucleotide primer to amplify
      a portion of plasmid pTrypHis

<400> SEQUENCE: 13
ccaagcttca ccatcaccat caccat                                        26

<210> SEQ ID NO 14
<211> LENGTH: 17
<212> TYPE: DNA
<213> ORGANISM: Artificial Sequence
<220> FEATURE:
<223> OTHER INFORMATION: Designed oligonucleotide primer to amplify
      a portion of plasmid pTrypSigTag

<400> SEQUENCE: 14
gcacagtcga ggctgat                                                  17

<210> SEQ ID NO 15
<211> LENGTH: 17
<212> TYPE: DNA
<213> ORGANISM: Artificial Sequence
<220> FEATURE:
<223> OTHER INFORMATION: Designed oligonucleotide primer to amplify
      a portion of plasmid pFBTrypSigTag

<400> SEQUENCE: 15
```

```
caaatgtggt atggctg                                             17
```

<210> SEQ ID NO 16
<211> LENGTH: 20
<212> TYPE: DNA
<213> ORGANISM: Artificial Sequence
<220> FEATURE:
<223> OTHER INFORMATION: Designed oligonucleotide primer to amplify
      active hBSSP6-encoding sequence

<400> SEQUENCE: 16

```
atcatcaagg gttatgagtg                                          20
```

<210> SEQ ID NO 17
<211> LENGTH: 28
<212> TYPE: DNA
<213> ORGANISM: Artificial Sequence
<220> FEATURE:
<223> OTHER INFORMATION: Designed oligonucleotide primer to amplify
      active hBSSP6-encoding sequence

<400> SEQUENCE: 17

```
cggaattcgc attaagaaga ggttggag                                 28
```

<210> SEQ ID NO 18
<211> LENGTH: 20
<212> TYPE: DNA
<213> ORGANISM: Artificial Sequence
<220> FEATURE:
<223> OTHER INFORMATION: Designed oligonucleotide primer designated
      as hBSSP6F1 for RACE f or human BSSP6 (forward)

<400> SEQUENCE: 18

```
tcaagccccg ctacatagtt                                          20
```

<210> SEQ ID NO 19
<211> LENGTH: 20
<212> TYPE: DNA
<213> ORGANISM: Artificial Sequence
<220> FEATURE:
<223> OTHER INFORMATION: Designed oligonucleotide primer designated
      as hBSSP6F2 for RACE f or human BSSP6 (forward)

<400> SEQUENCE: 19

```
atcatgctgg tgaagatggc                                          20
```

<210> SEQ ID NO 20
<211> LENGTH: 20
<212> TYPE: DNA
<213> ORGANISM: Artificial Sequence
<220> FEATURE:
<223> OTHER INFORMATION: Designed oligonucleotide primer designated
      as hBSSP6F3 to amplify full-length human brain BSSP6-encoding
      mRNA (forward)

<400> SEQUENCE: 20

```
ggactcaaga gaggaacctg                                          20
```

<210> SEQ ID NO 21
<211> LENGTH: 20
<212> TYPE: DNA
<213> ORGANISM: Artificial Sequence
<220> FEATURE:
<223> OTHER INFORMATION: Designed oligonucleotide primer designated as
      hBSSP6F4 to amplify mature human BSSP6-encoding region (forward)

<400> SEQUENCE: 21

```
atcatcaagg ggttcgagtg                                              20

<210> SEQ ID NO 22
<211> LENGTH: 20
<212> TYPE: DNA
<213> ORGANISM: Artificial Sequence
<220> FEATURE:
<223> OTHER INFORMATION: Designed oligonucleotide primer designated as
      hBSSP6F5 to amplify full-length human prostate BSSP6-encoding
      mRNA (forward)

<400> SEQUENCE: 22
ctgccttgct ccacacctgg                                              20

<210> SEQ ID NO 23
<211> LENGTH: 20
<212> TYPE: DNA
<213> ORGANISM: Artificial Sequence
<220> FEATURE:
<223> OTHER INFORMATION: Designed oligonucleotide primer designated as
      hBSSP6R1 for RACE for human BSSP6 (reverse)

<400> SEQUENCE: 23
ttctcacact tctggtgctc                                              20

<210> SEQ ID NO 24
<211> LENGTH: 20
<212> TYPE: DNA
<213> ORGANISM: Artificial Sequence
<220> FEATURE:
<223> OTHER INFORMATION: Designed oligonucleotide primer designated as
      hBSSP6R2 for RACE for human BSSP6 (reverse)

<400> SEQUENCE: 24
atggtgtctg tgatgttgcc                                              20

<210> SEQ ID NO 25
<211> LENGTH: 26
<212> TYPE: DNA
<213> ORGANISM: Artificial Sequence
<220> FEATURE:
<223> OTHER INFORMATION: Designed oligonucleotide primer designated as
      hBSSP6R3/P to amplify full-length human BSSP6-encoding mRNA
      (reverse)

<400> SEQUENCE: 25
aactgcagga accaaacacc aagtgg                                       26

<210> SEQ ID NO 26
<211> LENGTH: 20
<212> TYPE: DNA
<213> ORGANISM: Artificial Sequence
<220> FEATURE:
<223> OTHER INFORMATION: Designed oligonucleotide primer designated as
      mBSSP6F1 for RACE for mouse BSSP6 (forward)

<400> SEQUENCE: 26
cgacttcaac aacagcctcc                                              20

<210> SEQ ID NO 27
<211> LENGTH: 20
<212> TYPE: DNA
<213> ORGANISM: Artificial Sequence
<220> FEATURE:
<223> OTHER INFORMATION: Designated oligonucleotide primer designated as
      mBSSP6F2 for RACE for mouse BSSP6 (forward)
```

```
<400> SEQUENCE: 27
cttctttacc cgagctgtgc                                              20

<210> SEQ ID NO 28
<211> LENGTH: 20
<212> TYPE: DNA
<213> ORGANISM: Artificial Sequence
<220> FEATURE:
<223> OTHER INFORMATION: Designed oligonucleotide primer designated as
      mBSSP6F3 to amplify full-length mouse prostate BSSP6-encoding
      mRNA (forward)

<400> SEQUENCE: 28
taagctagga gaactgaggc                                              20

<210> SEQ ID NO 29
<211> LENGTH: 18
<212> TYPE: DNA
<213> ORGANISM: Artificial Sequence
<220> FEATURE:
<223> OTHER INFORMATION: Designed oligonucleotide primer designated as
      mBSSP6F4 to amplify mature mouse BSSP6-encoding region (forward)

<400> SEQUENCE: 29
atcaagggtt atgagtgc                                                18

<210> SEQ ID NO 30
<211> LENGTH: 19
<212> TYPE: DNA
<213> ORGANISM: Artificial Sequence
<220> FEATURE:
<223> OTHER INFORMATION: Designed oligonucleotide primer designated as
      mBSSP6F5 to amplify full-length mouse brain BSSP6-encoding mRNA
      (forward)

<400> SEQUENCE: 30
cttacaggct tggggattg                                               19

<210> SEQ ID NO 31
<211> LENGTH: 20
<212> TYPE: DNA
<213> ORGANISM: Artificial Sequence
<220> FEATURE:
<223> OTHER INFORMATION: Designed oligonucleotide primer designated as
      mBSSP6R1 for RACE for mouse BSSP6 (reverse)

<400> SEQUENCE: 31
gatgatgcct tgaagagatc                                              20

<210> SEQ ID NO 32
<211> LENGTH: 21
<212> TYPE: DNA
<213> ORGANISM: Artificial Sequence
<220> FEATURE:
<223> OTHER INFORMATION: Designed oligonucleotide primer designated as
      mBSSP6R2 for RACE for mouse BSSP6 (reverse)

<400> SEQUENCE: 32
catggtgtct gtgatgttgc c                                            21

<210> SEQ ID NO 33
<211> LENGTH: 28
<212> TYPE: DNA
<213> ORGANISM: Artificial Sequence
<220> FEATURE:
<223> OTHER INFORMATION: Designed oligonucleotide primer designated as
      mBSSP6R3/E to amplify full-length mouse BSSP6-encoding mRNA
```

(reverse)

<400> SEQUENCE: 33
cggaattcgc attaagaaga ggttggag                28

<210> SEQ ID NO 34
<211> LENGTH: 20
<212> TYPE: DNA
<213> ORGANISM: Artificial Sequence
<220> FEATURE:
<223> OTHER INFORMATION: Designed oligonucleotide primer designated as
      hBSSP6R3 to amplify a portion of BSSP6 variant type-encoding mRNA
      from human prostat
      ic cancer cell line PC-3 (reverse)

<400> SEQUENCE: 34
atggtgtctg tgatgttgcc                20

<210> SEQ ID NO 35
<211> LENGTH: 20
<212> TYPE: DNA
<213> ORGANISM: Artificial Sequence
<220> FEATURE:
<223> OTHER INFORMATION: Designed oligonucleotide primer designated as
      hBSSP6F7 to amplify a portion of human BSSP6-encoding mRNA
      (forward)

<400> SEQUENCE: 35
cctcaagccg tgggtgtcac                20

<210> SEQ ID NO 36
<211> LENGTH: 20
<212> TYPE: DNA
<213> ORGANISM: Artificial Sequence
<220> FEATURE:
<223> OTHER INFORMATION: Designed oligonucleotide primer to amplify
      conserved region of serin proteases-encoding sequence
<220> FEATURE:
<221> NAME/KEY: misc_feature
<222> LOCATION: (9)..(9)
<223> OTHER INFORMATION: n is a, c, g or t.
<220> FEATURE:
<221> NAME/KEY: misc_feature
<222> LOCATION: (12)..(12)
<223> OTHER INFORMATION: n is a, c, g or t.

<400> SEQUENCE: 36
gtgctcacng cngcbcaytg                20

<210> SEQ ID NO 37
<211> LENGTH: 20
<212> TYPE: DNA
<213> ORGANISM: Artificial Sequence
<220> FEATURE:
<223> OTHER INFORMATION: Designed oligonucleotide primer to amplify
      conserved region of serin proteases-encoding sequence
<220> FEATURE:
<221> NAME/KEY: misc_feature
<222> LOCATION: (12)..(12)
<223> OTHER INFORMATION: n is a, c, g or t.
<220> FEATURE:
<221> NAME/KEY: misc_feature
<222> LOCATION: (15)..(15)
<223> OTHER INFORMATION: n is a, c, g or t.

<400> SEQUENCE: 37
ccvctrwsdc cnccnggcga                20

<210> SEQ ID NO 38

```
<211> LENGTH: 117
<212> TYPE: DNA
<213> ORGANISM: Artificial Sequence
<220> FEATURE:
<223> OTHER INFORMATION: Designed oligonucleotide to construct plasmid
      pTrypHis

<400> SEQUENCE: 38
aagcttggct agcaacacca tgaatctact cctgatcctt acctttgttg ctgctgctgt    60
tgctgccccc tttcaccatc accatcacca tgacgacgat gacaaggatc cgaattc     117

<210> SEQ ID NO 39
<211> LENGTH: 117
<212> TYPE: DNA
<213> ORGANISM: Artificial Sequence
<220> FEATURE:
<223> OTHER INFORMATION: Designed oligonucleotide to construct plasmid
      pTrypHis

<400> SEQUENCE: 39
gaattcggat ccttgtcatc gtcgtcatgg tgatggtgat ggtgaaggg ggcagcaaca    60 gcagcagcaa caaaggtaag gatcaggagt agattcatgg tgttgctagc caagctt     117

<210> SEQ ID NO 40
<211> LENGTH: 5
<212> TYPE: PRT
<213> ORGANISM: Artificial Sequence
<220> FEATURE:
<223> OTHER INFORMATION: Synthetic

<400> SEQUENCE: 40

Asp Asp Asp Asp Lys
1               5

<210> SEQ ID NO 41
<211> LENGTH: 4
<212> TYPE: PRT
<213> ORGANISM: Artificial Sequence
<220> FEATURE:
<223> OTHER INFORMATION: Synthetic

<400> SEQUENCE: 41

Lys Val His Gly
1
```